(12) United States Patent
Felt et al.

(10) Patent No.: US 7,094,196 B2
(45) Date of Patent: Aug. 22, 2006

(54) FLUID SEPARATION METHODS USING A FLUID PRESSURE DRIVEN AND/OR BALANCED APPROACH

(75) Inventors: Thomas J. Felt, Boulder, CO (US); Dennis J. Hlavinka, Lakewood, CO (US)

(73) Assignee: Gambro Inc., Lakewood, CO (US)

( * ) Notice: Subject to any disclaimer, the term of this patent is extended or adjusted under 35 U.S.C. 154(b) by 241 days.

(21) Appl. No.: 10/708,856

(22) Filed: Mar. 29, 2004

(65) Prior Publication Data

US 2004/0164032 A1 Aug. 26, 2004

Related U.S. Application Data

(62) Division of application No. 10/008,989, filed on Nov. 2, 2001, now Pat. No. 6,736,768.

(60) Provisional application No. 60/245,282, filed on Nov. 2, 2000.

(51) Int. Cl.
*B01D 21/26* (2006.01)
(52) U.S. Cl. ........................................................ 494/37
(58) Field of Classification Search .................. 494/37, 494/41, 42, 45, 60, 63, 67, 81; 422/72; 210/781, 210/782, 787; 604/6.01, 6.02, 6.03, 6.04, 604/6.05, 6.06
See application file for complete search history.

(56) References Cited

U.S. PATENT DOCUMENTS

| 247,804 | A | 10/1881 | De Laval |
|---|---|---|---|
| 426,275 | A | 4/1890 | Hult et al. |
| 487,943 | A | 12/1892 | Beimling |
| 585,936 | A | 7/1897 | Linders |
| 748,038 | A | 12/1903 | Ayers |
| 3,145,713 | A | 8/1964 | Latham, Jr. |
| 3,304,990 | A | 2/1967 | Ontko et al. |
| 3,311,296 | A | 3/1967 | Torobin |
| 3,489,145 | A | 1/1970 | Judson et al. |
| 3,519,201 | A | 7/1970 | Eisel et al. |
| 3,655,123 | A | 4/1972 | Judson et al. |
| 3,737,096 | A | 6/1973 | Jones et al. |
| 3,747,843 | A | 7/1973 | Joyce et al. |
| 3,748,101 | A | 7/1973 | Jones et al. |

(Continued)

FOREIGN PATENT DOCUMENTS

DE 26 58 926 12/1976

(Continued)

OTHER PUBLICATIONS

IBM Technical Disclosure Bulletin NN7407404, "Plasmapheresis System", Jul. 1974, vol. 17:2, pp. 404-405.

(Continued)

*Primary Examiner*—David Sorkin
(74) *Attorney, Agent, or Firm*—John R. Merkling; Edria M. O'Connor; Laura B. Arciniegas

(57) ABSTRACT

The method separates a composite fluid, such as blood, into the components thereof in a centrifugal separation device. The fluid is delivered to a fluid receiving area in a rotor from which area the fluid travels through a radial inlet channel having an inlet channel height to a proximal end of a circumferential fluid separation channel. Near a distal end of the separation channel, fluid components travel into distinct first and second outlet channels. The height of the first channel is greater than the height of the more distal second channel. The inlet channel height is greater than the height of the first channel. The rotor may be balanced by axially symmetrical sets of inlet channels, separation channels and outlet channels or by a balance channel connected to the separation channel but displaced from the outlet channels.

24 Claims, 19 Drawing Sheets

U.S. PATENT DOCUMENTS

| | | |
|---|---|---|
| 3,825,175 A | 7/1974 | Sartory |
| 3,843,046 A | 10/1974 | Joyce |
| 3,864,089 A | 2/1975 | Tiffany et al. |
| 3,880,592 A | 4/1975 | Kelly et al. |
| 3,955,755 A | 5/1976 | Breillatt, Jr. et al. |
| 3,957,197 A | 5/1976 | Sartory et al. |
| 3,986,442 A | 10/1976 | Khoja et al. |
| 4,007,871 A | 2/1977 | Jones et al. |
| 4,010,894 A | 3/1977 | Kellogg et al. |
| 4,018,304 A | 4/1977 | Lolachi et al. |
| 4,059,108 A | 11/1977 | Latham, Jr. |
| 4,086,924 A | 5/1978 | Latham, Jr. |
| 4,091,989 A | 5/1978 | Schltz |
| 4,094,461 A | 6/1978 | Kellogg et al. |
| 4,108,353 A | 8/1978 | Brown |
| 4,109,852 A | 8/1978 | Brown et al. |
| 4,109,854 A | 8/1978 | Brown |
| 4,109,855 A | 8/1978 | Brown et al. |
| 4,111,356 A | 9/1978 | Boggs et al. |
| 4,113,173 A | 9/1978 | Lolachi |
| 4,114,802 A | 9/1978 | Brown et al. |
| 4,120,448 A | 10/1978 | Cullis |
| 4,120,449 A | 10/1978 | Brown et al. |
| 4,146,172 A | 3/1979 | Cullis et al. |
| 4,164,318 A | 8/1979 | Boggs |
| 4,185,629 A | 1/1980 | Cullis et al. |
| 4,187,979 A | 2/1980 | Cullis et al. |
| 4,191,182 A | 3/1980 | Popovich et al. |
| 4,194,684 A | 3/1980 | Boggs |
| 4,216,770 A | 8/1980 | Cullis et al. |
| 4,226,669 A | 10/1980 | Vilardi |
| 4,245,383 A | 1/1981 | Boggs |
| 4,303,193 A | 12/1981 | Latham, Jr. |
| 4,304,357 A | 12/1981 | Schoendorfer |
| 4,330,080 A | 5/1982 | Mathieu |
| 4,332,351 A | 6/1982 | Kellogg et al. |
| 4,342,420 A | 8/1982 | Rosemeier et al. |
| 4,379,452 A | 4/1983 | DeVries |
| 4,386,730 A | 6/1983 | Mulzet |
| 4,387,848 A | 6/1983 | Kellogg et al. |
| 4,402,680 A | 9/1983 | Schoendorfer |
| 4,416,654 A | 11/1983 | Schoendorfer et al. |
| 4,416,778 A | 11/1983 | Rogers |
| 4,417,884 A | 11/1983 | Schoendorfer et al. |
| 4,421,503 A | 12/1983 | Latham, Jr. et al. |
| 4,425,112 A | 1/1984 | Ito |
| 4,430,072 A | 2/1984 | Kellogg et al. |
| 4,435,293 A | 3/1984 | Graham, Jr. et al. |
| 4,436,631 A | 3/1984 | Graham, Jr. et al. |
| 4,439,178 A | 3/1984 | Mulzet |
| 4,447,221 A | 5/1984 | Mulzet |
| 4,464,167 A | 8/1984 | Schoendorfer et al. |
| 4,482,342 A | 11/1984 | Lueptow et al. |
| 4,526,515 A | 7/1985 | DeVries |
| 4,531,932 A | 7/1985 | Luppi et al. |
| 4,557,719 A | 12/1985 | Neumann et al. |
| 4,610,846 A | 9/1986 | Martin |
| 4,636,193 A | 1/1987 | Cullis |
| 4,637,813 A | 1/1987 | DeVries |
| 4,647,279 A | 3/1987 | Mulzet et al. |
| 4,670,147 A | 6/1987 | Schoendorfer et al. |
| 4,675,106 A | 6/1987 | Schoendorfer et al. |
| 4,675,117 A | 6/1987 | Neumann et al. |
| 4,696,666 A | 9/1987 | Rice, Jr. |
| 4,708,712 A | 11/1987 | Mulzet |
| 4,713,176 A | 12/1987 | Schoendorfer et al. |
| 4,734,089 A | 3/1988 | Cullis |
| 4,738,655 A | 4/1988 | Brimhall et al. |
| 4,740,313 A | 4/1988 | Schoendorfer et al. |
| 4,753,729 A | 6/1988 | Schoendorfer et al. |
| 4,755,300 A | 7/1988 | Fischel et al. |
| 4,776,964 A | 10/1988 | Schoendorfer et al. |
| 4,790,807 A | 12/1988 | Neumann et al. |
| 4,804,363 A | 2/1989 | Valeri |
| 4,806,247 A | 2/1989 | Schoendorfer et al. |
| 4,816,151 A | 3/1989 | Schoendorfer et al. |
| 4,824,431 A | 4/1989 | McAlister |
| 4,834,890 A | 5/1989 | Brown et al. |
| 4,850,995 A | 7/1989 | Tie et al. |
| 4,850,998 A | 7/1989 | Schoendorfer |
| 4,851,126 A | 7/1989 | Schoendorfer |
| 4,869,812 A | 9/1989 | Schoendorfer et al. |
| 4,879,040 A | 11/1989 | Prince et al. |
| 4,889,524 A | 12/1989 | Fell et al. |
| 4,911,833 A | 3/1990 | Schoendorfer et al. |
| 4,919,817 A | 4/1990 | Schoendorfer et al. |
| 4,934,995 A | 6/1990 | Cullis |
| 4,935,002 A | 6/1990 | Gordon |
| 4,940,543 A | 7/1990 | Brown et al. |
| 4,943,273 A | 7/1990 | Pages |
| 4,944,883 A | 7/1990 | Schoendorfer et al. |
| 4,968,295 A | 11/1990 | Neumann |
| 4,983,158 A | 1/1991 | Headley |
| 4,990,132 A | 2/1991 | Unger et al. |
| 5,006,103 A | 4/1991 | Bacehowski et al. |
| 5,034,135 A | 7/1991 | Fischel |
| 5,045,048 A | 9/1991 | Kaleskas et al. |
| 5,053,121 A | 10/1991 | Schoendorfer et al. |
| 5,053,127 A | 10/1991 | Schoendorfer et al. |
| 5,061,381 A | 10/1991 | Burd |
| 5,104,526 A | 4/1992 | Brown et al. |
| RE33,924 E | 5/1992 | Valeri |
| 5,114,396 A | 5/1992 | Unger et al. |
| 5,135,667 A | 8/1992 | Schoendorfer |
| 5,147,290 A | 9/1992 | Jonsson |
| 5,171,456 A | 12/1992 | Hwang et al. |
| 5,186,844 A | 2/1993 | Burd et al. |
| 5,188,583 A | 2/1993 | Guigan |
| 5,194,145 A | 3/1993 | Schoendorfer |
| 5,211,808 A | 5/1993 | Vilardi et al. |
| 5,217,426 A | 6/1993 | Bacehowski et al. |
| 5,217,427 A | 6/1993 | Cullis |
| 5,260,598 A | 11/1993 | Brass et al. |
| 5,275,731 A | 1/1994 | Jahn |
| 5,281,342 A | 1/1994 | Biesel et al. |
| 5,295,953 A | 3/1994 | Richard et al. |
| 5,298,171 A | 3/1994 | Biesel |
| 5,370,802 A | 12/1994 | Brown |
| 5,376,263 A | 12/1994 | Fischel |
| 5,405,308 A | 4/1995 | Headley et al. |
| 5,421,812 A | 6/1995 | Langley et al. |
| 5,445,593 A | 8/1995 | Biesel et al. |
| 5,464,534 A | 11/1995 | Fischel |
| 5,494,592 A | 2/1996 | Latham, Jr. et al. |
| 5,571,068 A | 11/1996 | Bacehowski et al. |
| 5,605,842 A | 2/1997 | Langley et al. |
| 5,607,579 A | 3/1997 | Latham, Jr. et al. |
| 5,607,830 A | 3/1997 | Biesel et al. |
| 5,611,997 A | 3/1997 | Langley et al. |
| 5,614,106 A | 3/1997 | Payrat et al. |
| 5,651,766 A | 7/1997 | Kingsley et al. |
| 5,653,887 A | 8/1997 | Wahl et al. |
| 5,674,173 A | 10/1997 | Hlavinka et al. |
| 5,702,357 A | 12/1997 | Bainbridge et al. |
| 5,704,888 A | 1/1998 | Hlavinka et al. |
| 5,704,889 A | 1/1998 | Hlavinka et al. |
| 5,722,926 A | 3/1998 | Hlavinka et al. |
| 5,723,050 A | 3/1998 | Unger et al. |
| 5,728,060 A | 3/1998 | Kingsley et al. |
| 5,733,253 A | 3/1998 | Headley et al. |
| 5,738,644 A | 4/1998 | Holmes et al. |
| 5,738,792 A | 4/1998 | Schoendorfer |
| 5,779,660 A | 7/1998 | Kingsley et al. |
| 5,783,085 A | 7/1998 | Fischel |

| | | |
|---|---|---|
| 5,792,038 A | 8/1998 | Hlavinka |
| 5,853,382 A | 12/1998 | Kingsley et al. |
| 5,876,321 A | 3/1999 | Hlavinka et al. |
| 5,882,289 A | 3/1999 | Sakota et al. |
| 5,885,239 A | 3/1999 | Headley et al. |
| 5,904,355 A | 5/1999 | Powers |
| 5,939,319 A | 8/1999 | Hlavinka et al. |
| 5,951,877 A | 9/1999 | Langley et al. |
| 5,954,626 A | 9/1999 | Hlavinka |
| 6,007,509 A | 12/1999 | Kingsley et al. |
| 6,019,742 A | 2/2000 | Headley et al. |
| 6,039,711 A | 3/2000 | Headley et al. |
| 6,053,856 A | 4/2000 | Hlavinka |
| 6,062,078 A | 5/2000 | Meisberger |
| 6,074,335 A | 6/2000 | Headley et al. |
| 6,099,491 A | 8/2000 | Headley et al. |
| 6,102,883 A | 8/2000 | Kingsley et al. |
| 6,200,287 B1 | 3/2001 | Keller et al. |
| 6,221,315 B1 | 4/2001 | Giesler et al. |
| 6,261,217 B1 | 7/2001 | Unger et al. |
| 6,273,849 B1 | 8/2001 | Scherer |
| 6,277,060 B1 | 8/2001 | Neumann |
| 6,280,375 B1 | 8/2001 | Meisberger et al. |
| 6,296,602 B1 | 10/2001 | Headley |
| 6,312,372 B1 | 11/2001 | Larsson et al. |
| 6,315,707 B1 | 11/2001 | Smith et al. |
| 6,319,471 B1 | 11/2001 | Langley et al. |
| 6,322,488 B1 | 11/2001 | Westberg et al. |
| 6,325,775 B1 | 12/2001 | Thom et al. |
| 6,334,842 B1 | 1/2002 | Hlavinka et al. |
| 6,736,768 B1 * | 5/2004 | Felt et al. ............ 494/60 |
| 6,773,389 B1 * | 8/2004 | Hlavinka et al. ...... 494/60 |

FOREIGN PATENT DOCUMENTS

| | | |
|---|---|---|
| DE | 38 17 664 | 11/1989 |
| EP | 0 096217 | 2/1983 |
| EP | 0 214803 | 3/1987 |
| EP | 1043072 | 10/2000 |
| JP | 55086552 | 6/1980 |
| WO | PCT/US95/13447 | 4/1996 |
| WO | PCT/US96/03018 | 12/1996 |
| WO | WO 00/44502 | 8/2000 |
| WO | PCT/US00/06561 | 9/2000 |
| WO | PCT/US00/06945 | 9/2000 |

OTHER PUBLICATIONS

International Search Report PCT/US 01/46953.
International Search Report PCT/US 95/13447.
Schoendorfer, D.W., "Automation in Apheresis", pp. 129-146, undated.

* cited by examiner

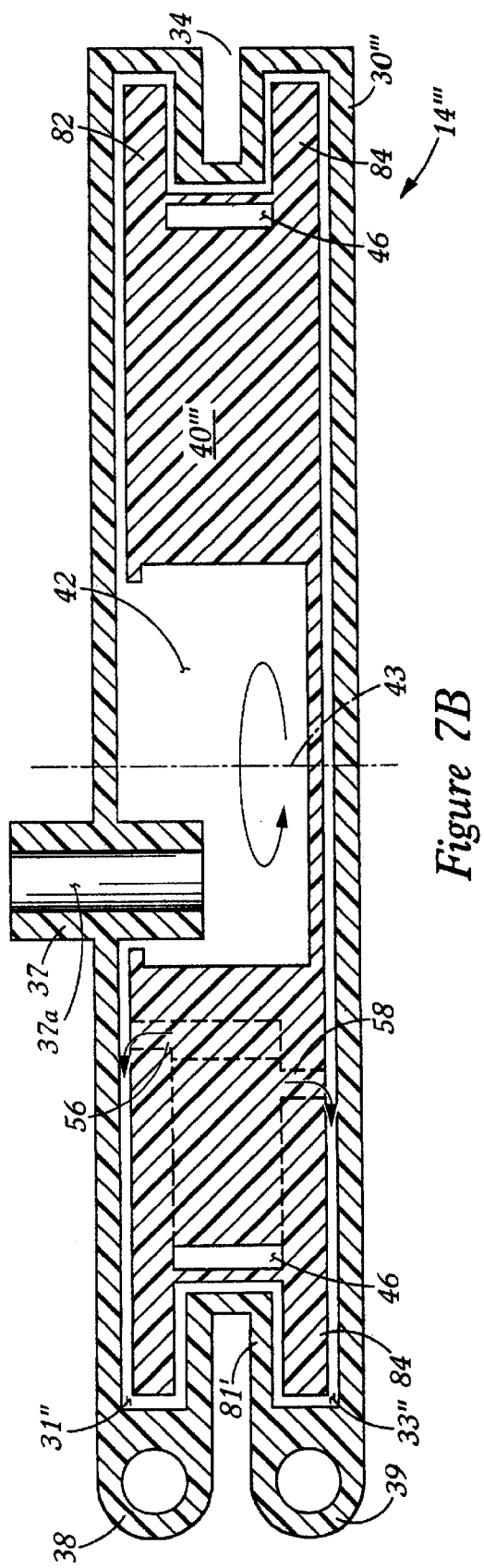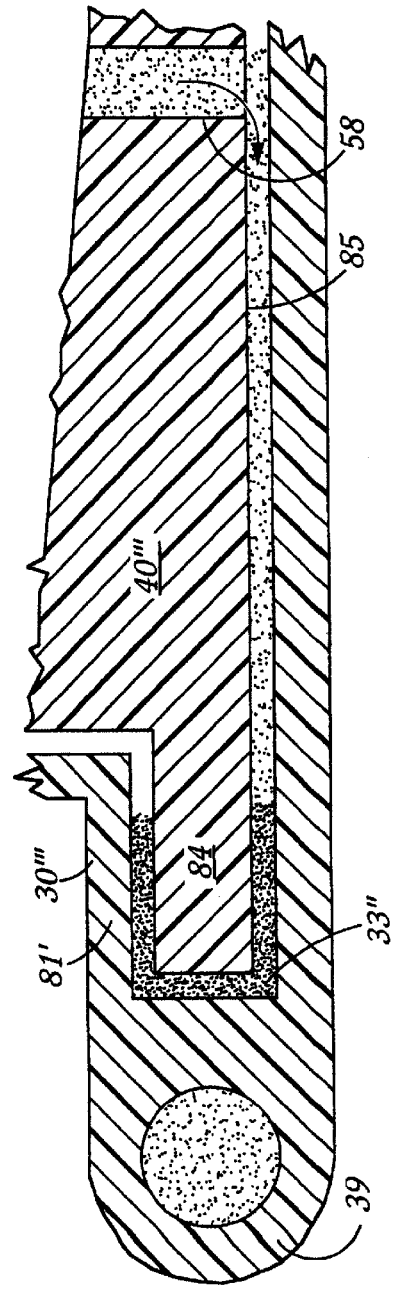

FLUID SEPARATION METHODS USING A FLUID PRESSURE DRIVEN AND/OR BALANCED APPROACH

CROSS REFERENCE TO RELATED APPLICATIONS

This application is a divisional of U.S. application Ser. No. 10/008,989, files 02 Nov. 2001, now U.S. Pat. No. 6,736,768, which claims the benefit of U.S. provisional application No. 60/245,282, filed 02 Nov. 2000.

BACKGROUND OF INVENTION

The present invention is directed generally to centrifugal fluid separation devices and is more particularly concerned with a pressure driven and/or balanced separation device preferably having a disposable, non-invasively driven, loopless rotor disposed in a rotating-sealless relationship with the entry and exit flow tubing lines.

A number of fluid separation devices have been known and various models are currently available for the separation of blood or other composite fluids into the various component elements thereof. For example, a variety of centrifugal machines are available for separating blood into component elements such as red blood cells, platelets and plasma, among others.

Centrifugation for such purposes has come in many forms in both continuous and batch types. For example, in the widely used process known as continuous centrifugation, as generally opposed to batch process centrifugation, a continuous input of a composite fluid is flowed into the separation device or chamber while at the same time the components of that composite fluid are substantially continuously separated and these separated components are usually then also substantially continuously removed therefrom. Many currently popular forms of such continuous fluid separation devices include loops of entry and exit flow tubing lines connected to the separation centrifuge chamber such that each loop is rotated in a relative one-omega–two-omega ($1\omega$–$2\omega$) relationship to the centrifuge chamber itself so that the tubing lines will remain free from twisting about themselves.

An alternative form of tubing line connection to a continuous centrifugal separation device is also available in the art which does not have such a loop, but which instead requires one or more rotating seals at the respective connections of the tubing line or lines to the centrifuge separation chamber, again to maintain the tubing lines free from twisting.

Batch-type centrifugation, on the other hand, usually involves separation of a composite fluid such as whole blood in a closed container, often a deformable bag, followed by a usually complicated process of automated and/or manual expression of one or more of the separated components out of the separation container or bag. A great deal of control, either automated, such as by optical interface detection, or by a diligent human operator watching a moving interface, is required with such previous batch-type processes. Indeed, various means and methods have been used in prior centrifugal separation devices both continuous and batch, for driving fluid flow and for maintaining desirable interface position control between the component elements being separated thereby. For example, as mentioned, many optical control feedback methods and devices have been employed in the art. Various pumping and valving arrangements are also used in various of these and other systems. Alternative, relatively automatic volume flow and density relationship interface controls have also been used. For example, in a continuous system, control outlet ports may be disposed in strategic locations relative to the separated component outlet ports.

Nevertheless, many facets of these prior separation devices, though satisfactorily productive, may provide certain features which are less efficient than a desired optimum. For example, centrifugal separation devices using loops of tubing lines rotated in the above-described $1\omega$–$2\omega$ relationship with the centrifuge separation chamber generally require significant, usually large drive mechanisms which thereby mandate that each such entire device then also be necessarily of a relatively large scale. Rotating seal devices, on the other hand, require intricate and often operationally problematic rotating seal structures. Sterility may also be an obstacle for rotating seals. Still further, many prior drive and/or interface control systems have either been overly complex as in the case of most of the optical control models, and/or automatic volume flow/density controls may not be as desirably efficient in separation due to the usually inherent re-mixing of some quantities of the centrifugally separated components.

Hence, substantial desiderata remain to provide more highly efficient centrifugal separation devices in terms of increased efficiency fluid flow drive and separation interface controls; reduced rotor drive mechanization, quantity and/or scale; and/or reduced seal need and/or intricacy. It is toward any one or more of these or other goals as may be apparent throughout this specification that the present invention is directed.

SUMMARY OF INVENTION

The present invention is directed generally to centrifugal separation devices and/or systems for use in centrifugally separating composite fluids into the component elements thereof. Such centrifugal separation devices and/or systems include unique centrifugal rotor and rotor housing combinations in which each rotor may be disposed in a freely rotatable disposition relative to the rotational device housing. Freely rotatable indicates loopless and rotating sealless as well as a preference that these rotors may be magnetically or otherwise non-invasively driven. A totally closed system may thus be provided with simple sterilization and disposability of the rotor and/or the rotor/housing combination and/or the tubing set associated therewith.

Each rotor has a substantially central fluid receiving/containing area and several fluid flow channels defined therein. In a preferred embodiment, a composite fluid to be separated into component parts may then be delivered to the fluid receiving area from which it may travel under centrifuge conditions through a fluid transport channel to a circumferential fluid separation channel where it may be subjected to substantial centrifugal forces which may separate the composite fluid into respective components. These components may then travel to distinct first and second separated fluid outlet channels. The separated fluid components may then exit from these outlet channels and may then be moved from the separation device to a collection bag for storage or further processing or may then be returned to the donor. The composite fluid may be of various sorts, but is preferably whole blood, and the respective components may then be plasma and red blood cells (RBCs), although buffy coats and/or platelets, among others, may also be separated and harvested herewith.

The inlet channel and the first and second fluid outlet channels are preferably pre-selected to have respective inlet and first and second outlet lengths or "heights" (or relative radial distances) that are selected to be related to each other so as to provide a substantial hydraulic or hydrostatic fluid pressure balance between the outlets for the respective separated fluids flowing therethrough. Such a pressure relationship provides for forcing the fluid flow and the outlet balance preferably controls the desired location of the interface between the separated fluid components within the circumferential separation channel. The preferred outlet channel length or height relationship which provides this hydraulic balance may be derived from the general hydrostatic equation $\rho_2 g_2 h_2 = \rho_3 g_3 h_3$ wherein the length or height of the first outlet channel in this equation is $h_2$, and the length or height of the second outlet channel is $h_3$. These relative lengths or heights, $h_2$ and $h_3$, may then be selected so as to provide the appropriate preferred pressure balance given a separating composite fluid to be flowed in separated fluid component parts therethrough. The other variables in the above equation are either fluid dependent, see e.g., $\rho_2$ and $\rho_3$ which represent the respective densities of the separated fluids in the first and second outlet channels, or are otherwise relatively non-selectable and/or for the most part not as consequential or are relatively non-governing in the general equation, e.g., the $g_2$ and $g_3$ variables are gravitational or centrifugal acceleration values preferably representing the respective average g value in each of the two columns, which may be a similar, if not a substantially equal value (i.e., even though there is likely a distinction, $g_2$ may generally vary a relatively small amount from $g_3$) in normal operation. Hence, the dominant, selectable driving differences will be in the relative heights $h_2$ and $h_3$ which may simply be chosen to accommodate for any differences in the other terms, $\rho$ or Thus, for a composite fluid such as whole blood, where the respective densities of the separable component parts, e.g., plasma and RBCs, are known (within sufficiently controllable ranges), then the respective heights, $h_2$ and $h_3$ may be chosen to appropriately set the location of the interface of separated components therebetween. This interface will thus remain where desired, preferably in the separation channel notwithstanding a substantially continuous inflow of composite fluid to be separated and a substantially continuous outflow of separated components.

Other similarly derived relationships of interest particularly relative to the dynamic forcing of the fluid flow in this invention, among others, are also involved in the systems of the present invention. For example, a further preferred aspect of the present invention involves a preferred relationship between either of the outlet fluid pressure term(s) and the inlet pressure term, particularly as these are impacted by the selection of the outlet channel heights or lengths $h_2$ and $h_3$ as described above, as well as the selection of the inlet channel height or length$_1$. Here, the fluid will flow in a continuous forward fashion so long as the inlet fluid pressure term $\rho_1 g_1 h_1$ is at least greater than either of the outlet fluid pressure terms $\rho_2 g_2 h_2$ or $\rho_3 g_3 h_3$. In an equation form, this relationship is $\rho_1 g_1 h_1 > \rho_2 g_2 h_2$ or $\rho_3 g_3 h_3$.

This relationship governs a general forcing of the fluid flow in one direction out of the initial receiving/containment area, into the separation channel and from there, into the respective component collection areas. In the preferred embodiment where $\rho_2 g_2 h_2 = \rho_3 g_3 h_3$, then the inlet pressure term $\rho_1 g_1 h_1$ will be greater than both of the outlet pressure terms simultaneously.

It is to be understood that both the foregoing general description and the following detailed description are exemplary, and are intended merely to provide limited explanation of the preferred embodiments of the invention as more broadly claimed. These and further aspects of the present invention will become clearer from the detailed description read in concert with the drawings in which like component elements are referenced therein with like component numbers throughout the several views.

BRIEF DESCRIPTION OF DRAWINGS

FIGS. 7A, 7B, and 7C are cross-sectional views of still further alternative centrifuge units of alternative separation devices according to the present invention.

DETAILED DESCRIPTION

A pressure-balanced, loopless, sealless separation device according to the present invention is depicted in the attached drawings and identified by the general reference number 10 therein. Note, the processing of whole blood as the preferred composite fluid is described in the preferred embodiments herein although other composite fluids may also be processed hereby. Red blood cells (RBCs) and plasma are the primary preferred components described as separated from whole blood herein, although processing for the collection of buffy coats, platelets or white blood cells, among others, may also be accomplished herewith.

Figure 1A:
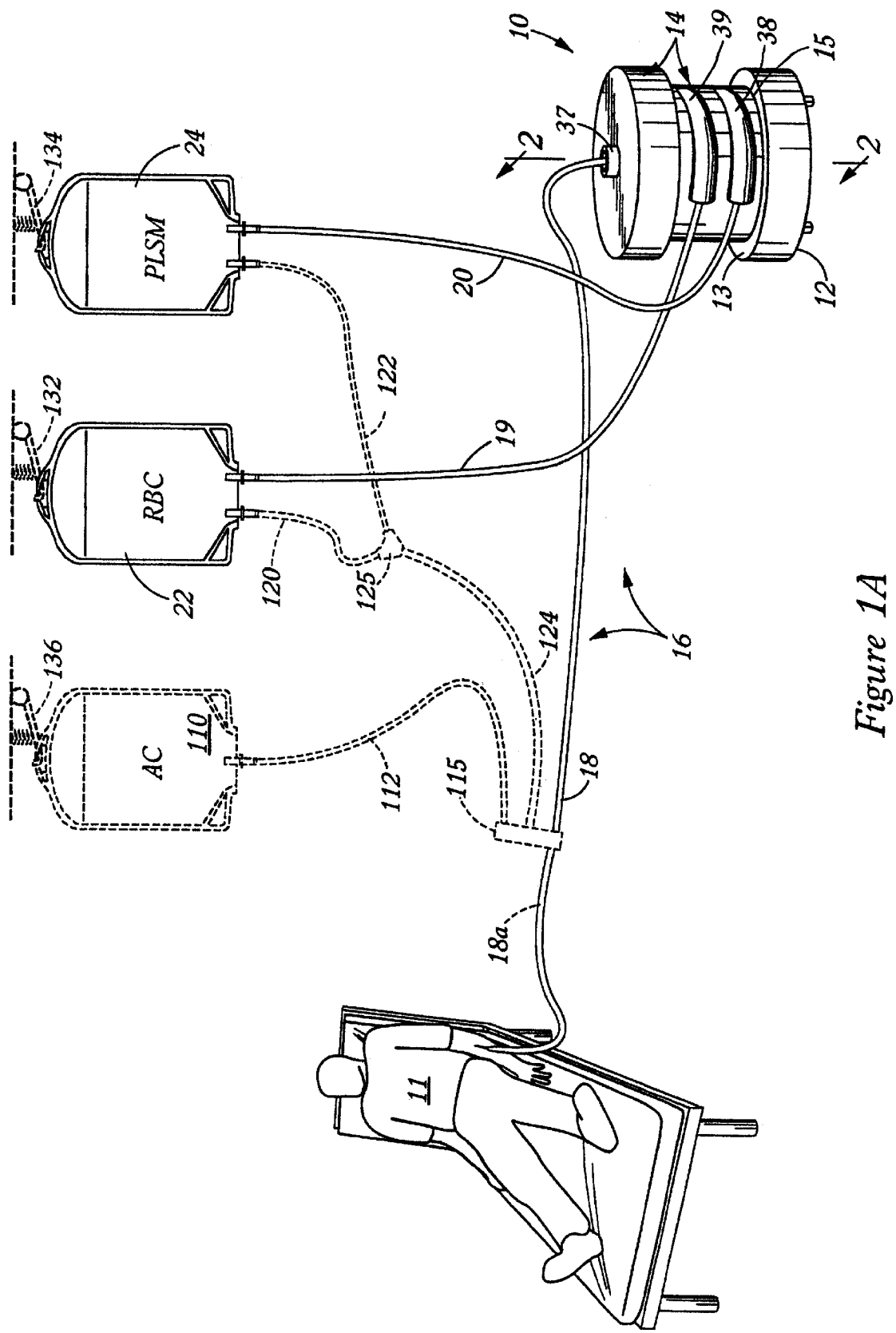
FIG. 1A is an isometric schematic view of a separation device and/or system of the present invention as connected with fluid containers and a human donor.

As shown for example in FIG. 1A in relation to a donor 11, a separation device 10 may generally include a motor base 12 and a centrifuge unit 14 with a tubing system 16 having one or more tubing lines 18, 19, 20 (shown in solid lines) and associated collection or storage reservoirs or bags 24. These primary component parts and a few optional tubing lines and associated optional components which are shown in dashed lines in FIG. 1A and in solid and dashed lines in FIG. 1B will be further described below. Note, the option of using an anticoagulant (to be described in more detail relative to FIG. 1B) would be preferred, if not necessary in a direct donor draw like that shown in FIGS. 1A and 1B. However, the composite fluid source may be other than a live donor or patient such as the donor/patient 11 shown, and could be a bag or other composite fluid container.

In the preferred embodiment, the motor base 12, which may also be referred to as the drive portion of the separation device 10, is preferably a table-top sized, simply transportable magnetic (or other drive-type) apparatus which in the magnetic embodiment creates a spinning magnetic field. The motor base 12 may create this spinning magnetic field by, for example, physically spinning or rotating one or more magnets disposed therein about a rotational axis defined vertically therethrough, or, the magnetic field could be created alternatively by charging one or more magnets, or electromagnetic coils, in a controlled rotational sequence as is known generally in the industry. Other alternative drive mechanisms which are preferably non-invasive, may also be used.

In any case, the centrifuge unit 14, which may also be referred to as the centrifuge portion or part of the separation device 10, is preferably a self-contained and disposable unit which readily mates with the motor base 12. A preferred, readily mating relationship is as follows. Motor base 12 is preferably a flat-topped device which generates a spinning magnetic field that emanates out of the flat-top surface 13 thereof. Centrifuge unit 14 is then a preferably flat-bottomed unit which may be readily placed or simply set upon the flat-top surface 13 of motor base 12 in operative relationship therewith. A preferably flat-bottomed surface 15 of unit 14 would thus be disposed in surface-to-surface contact with the top surface 13 of motor base 12. In the preferred embodiments, this surface-to-surface contact relationship is preferably substantially horizontal. The axis of rotation (see description relative to FIGS. 2, 3A and 3B, below) is preferably substantially perpendicular to the flat-top surface 13 of base 12 and to the flat-bottomed surface 15 of unit 14 and would thus be substantially vertical in the preferred embodiments shown and described herein.

Figure 1B:
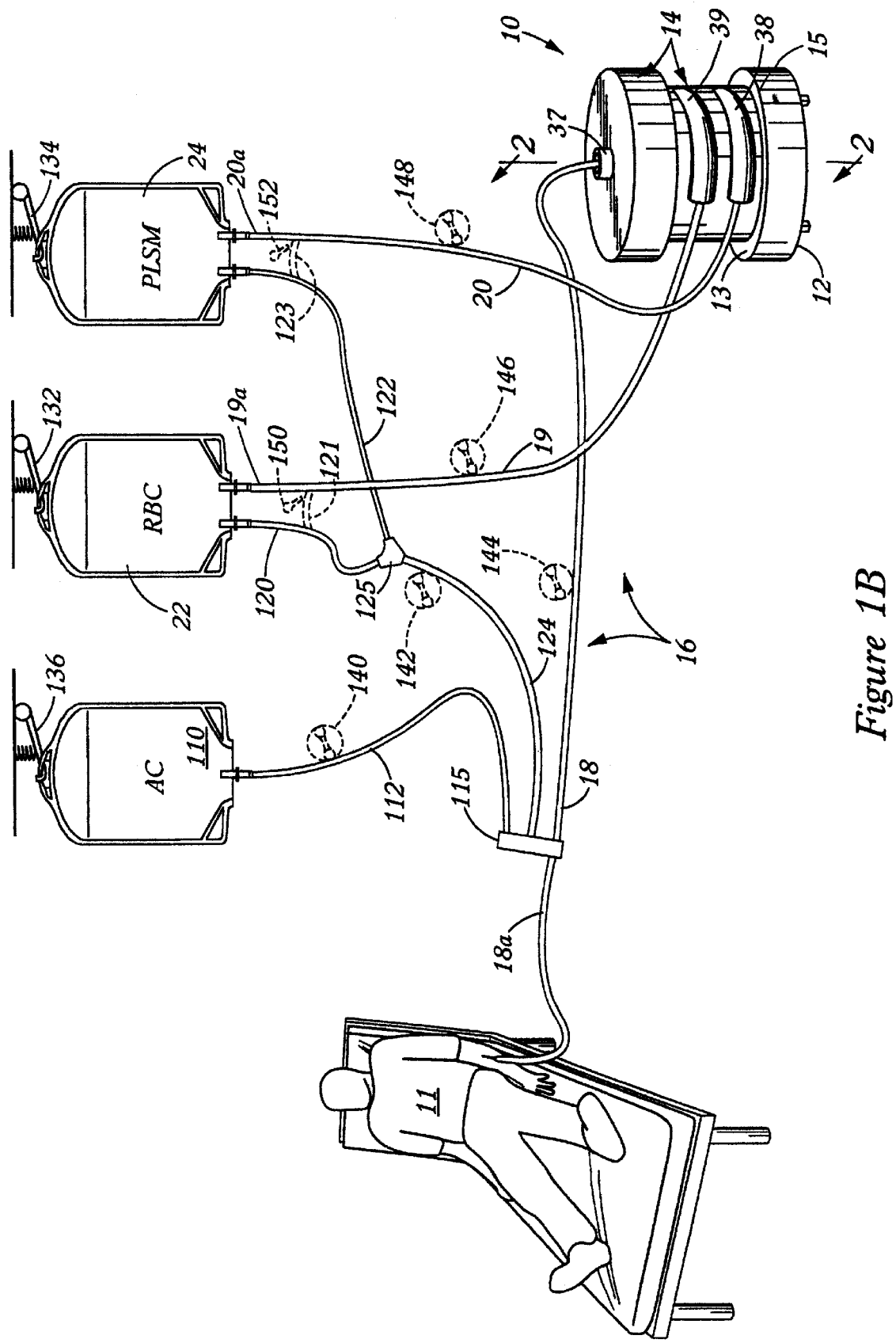
FIG. 1B is an isometric schematic view of a separation device and/or system like that in FIG. 1A shown with additional alternative flow components.
Figure 2:
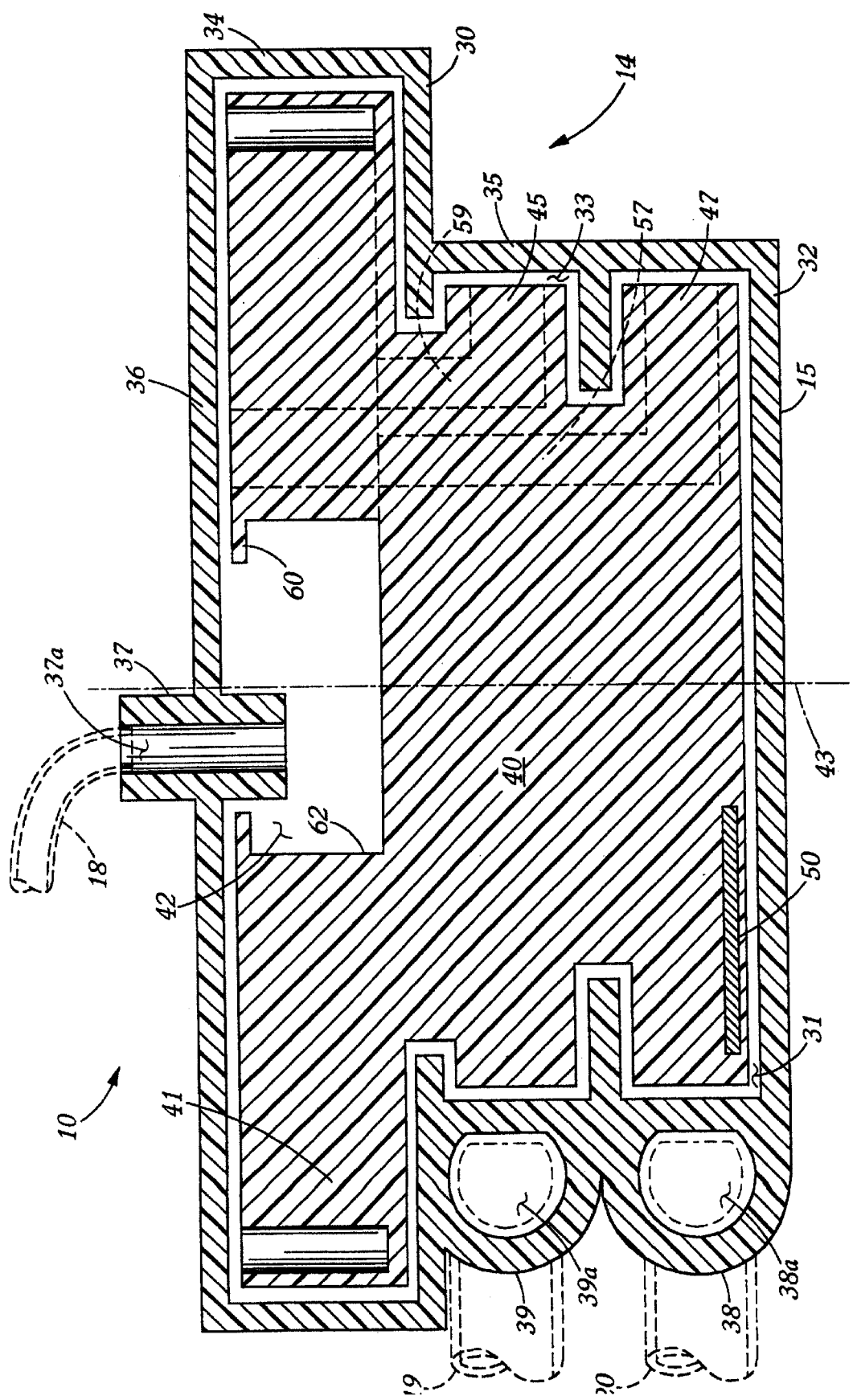
FIG. 2 is a cross-sectional view of a centrifuge unit of a separation device like that in FIGS. 1A and 1B taken along lines 2—2, thereof.

As depicted in more detail in FIG. 2, the centrifuge unit 14 generally includes an outer housing 30 and an internal rotor assemblage 40. In broad terms, the outer housing 30 includes a bottom wall 32 (the exterior face of which being the flat-bottom surface 15 described above), one or more circumferential walls 34, 35, and a top wall 36. Bottom, circumferential, and top walls 34, 35 and 36 are preferably contiguous (after assembly with a rotor 40) and may at least partially be integrally conjoined or formed, although they may each be separately-formed elements which are subsequently joined. In either case, the walls preferably form a fluid-tight arrangement. A fluid inlet aperture 37a is preferably defined in the top wall 36, and two exit 38a, 39a are preferably defined in, through and adjacent the lower circumferential wall 35. Respective inlet and outlet structures 37, 38 and 39 as shown are preferably used to define the respective apertures 37a, 38a and 39a, although other forms could be used. The tubing system 16 and respective fluid storage containers 22, 24 (not shown in FIG. 2) for example, are connected to the housing 30 as shown in FIGS. 1A and 1B (and in dashed lines in FIG. 2) via the connections of tubing lines 18, 19 and 20 with the respective aperture structures 37, 38 and 39 (tubings 18, 19 and 20 are the elements shown in dashed lines in FIG. 2).

Also as shown in FIG. 2, a preferred rotor 40 has three general layers; namely, a top-most layer where the separation is accomplished, an intermediate layer 45 where RBCs are collected for movement to a storage container (or back to the donor 11), and a lower layer 47 for collection of plasma. These layers will be described further below. Also note in FIG. 2 a piece of metallic material 50 is shown disposed within the lower layer 47. At least one such piece of metallic material 50 is preferably disposed therein to interact with the rotating magnetic field generated by the base to spin the rotor 40 about the rotational axis 43 (see description below) within the substantially stationary housing 30.

Figure 3C:
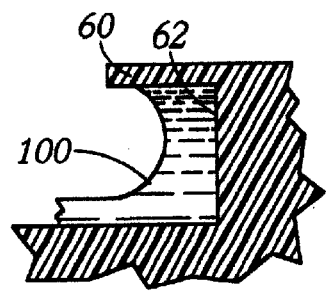
FIG. 3C is a broken-away, cross-sectional view of a portion of the separation layer of FIGS. 3A and 3B, taken along line 3C—3C thereof.
Figure 3A:
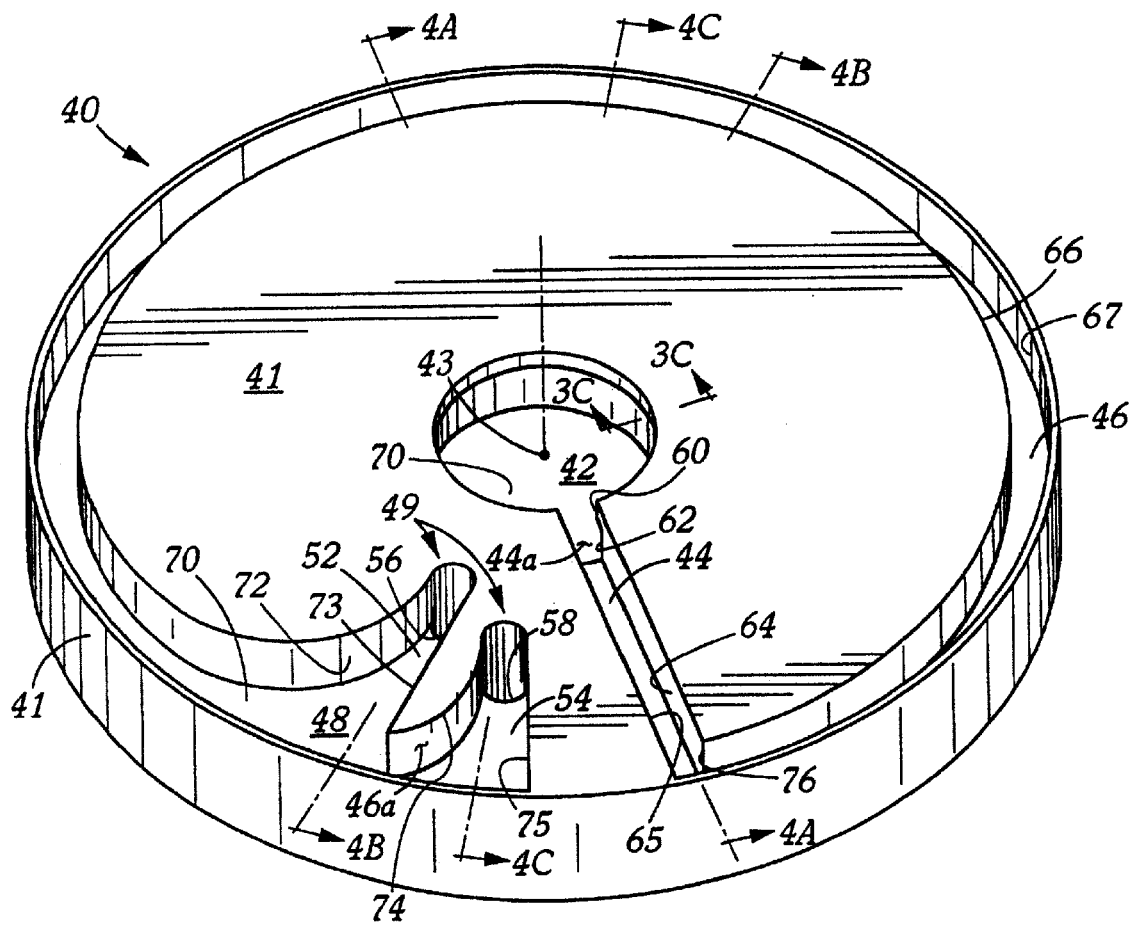
FIG. 3A is an isometric view of the separation layer of a centrifuge part of a separation device according to the present invention.
Figure 3B:
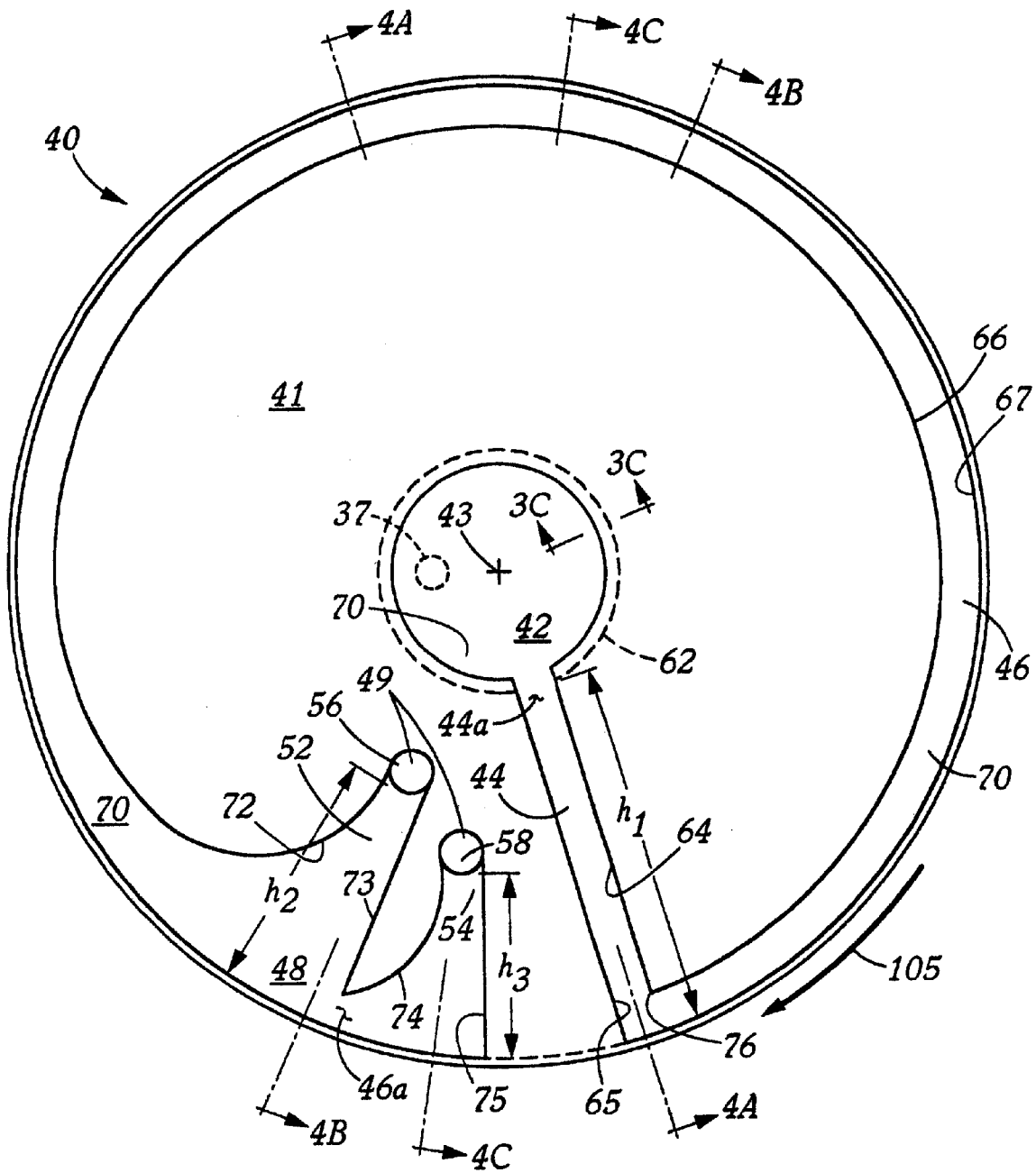
FIG. 3B is a plan view of the separation layer of FIG. 3A.
Figure 4A:
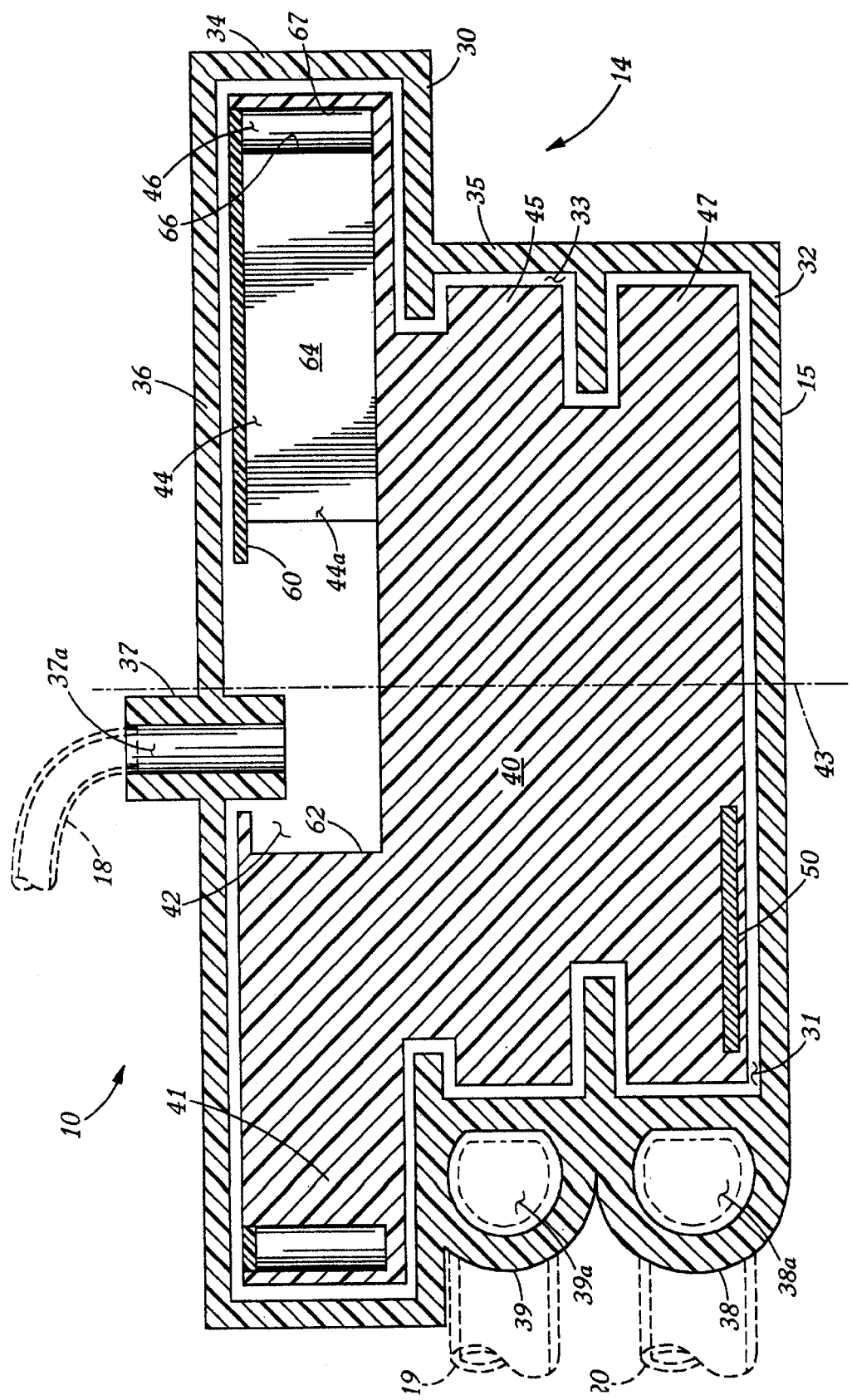
FIGS. 4A, 4B and 4C are cross-sectional views of the centrifuge unit of the separation device of FIGS. 3A and 3B taken along respective lines 4A—4A, 4B—4B, and 4C—4C, thereof.
Figure 4B:
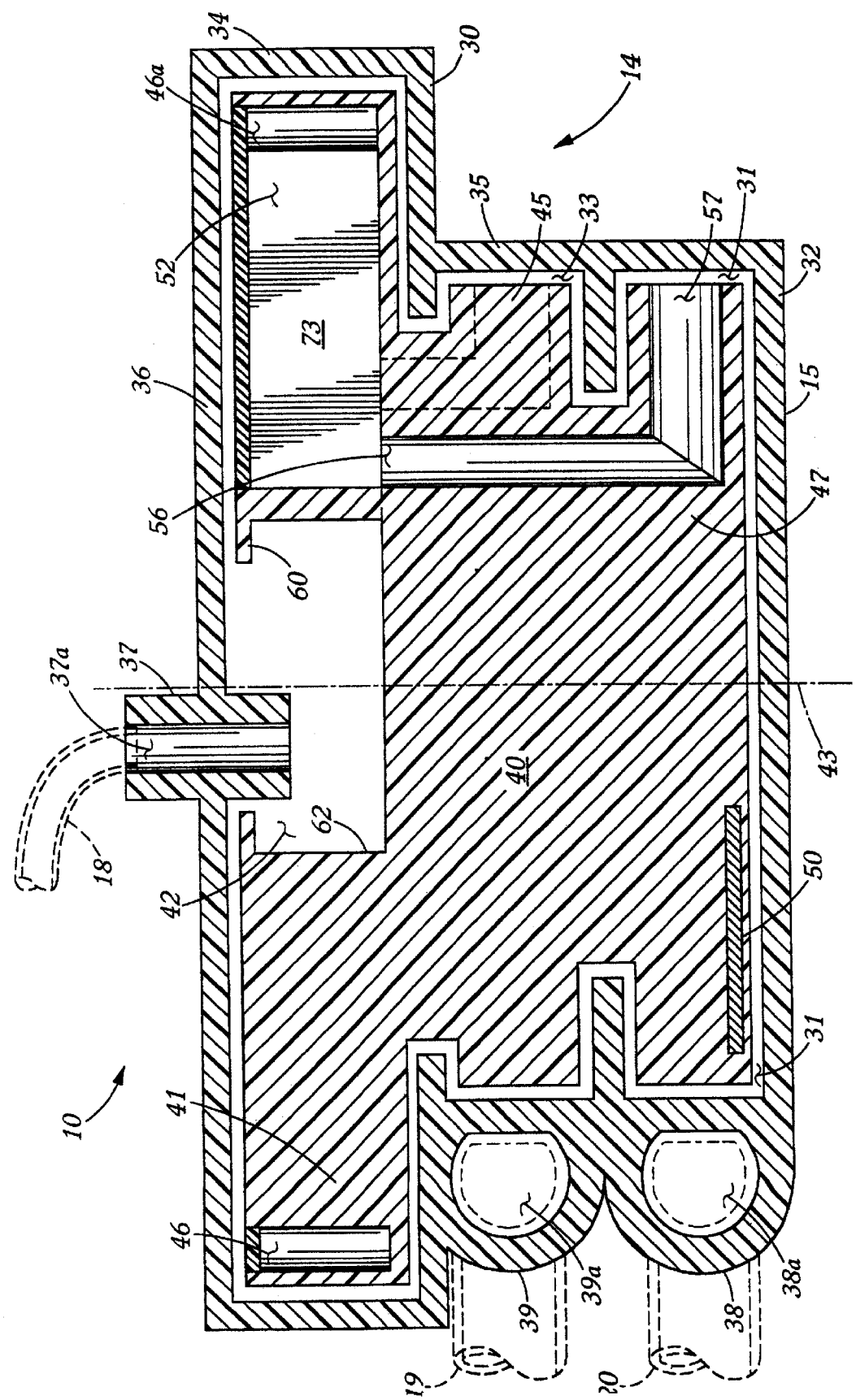

The top portion or layer 41 of a preferred internal rotor 40 of centrifuge unit 14 is shown separately in more detail in FIGS. 3A and 3B. In this embodiment, the top portion 41 may also be known as the separation layer of the centrifuge unit 14. As depicted here, the top portion 41 presents a fluid flow configuration preferably providing a fluid pressure drive and balance relationship for forcing fluid flow and improving interface control. Thus, the configuration includes a substantially central fluid receiving area 42 which is connected in fluid communication with a radial transport or inlet channel 44 via a radial inlet port 44a defined thereby. Transport channel 44 runs preferably radially outwardly to a substantially circumferential separation channel The adjective circumferential is intended here to indicate the channel which is at or near the circumference of the rotor 40, and traverses a path which is substantially circumferential there around, yet need not be of a constant radial distance from the rotor center. Transport channel 44 is open to and fluidly communicates with the circumferential separation channel 46. Circumferential channel 46 then runs from this intersection with the radial transport channel 44, substantially circumferentially around the periphery of rotor 40 to the separation and outlet regions 48, 49. Separation and outlet regions 49 will be described in further detail below; however, it should first be noted that the circumferential separation channel 46 is also in fluid communication therewith, and particularly communication with both of the two separate outlet channels 52, 54 defined here between the separation and outlet regions 48, 49. A preferably short continuation portion 46a of circumferential channel may be defined as continuing between the first outlet channel 52 and the second outlet channel 54 and providing fluid communication therebetween. Outlet channel 52 then connects to an outlet aperture 56 and channel 54 similarly connects to an outlet aperture 58. These and other features are shown also in FIGS. 4A–4C. For example, a cross-sectional view of the radial transport channel 44 is shown in FIG. 4A as it leads from the fluid receiving area 42 to the circumferential channel 46. FIG. 4B shows a cross-sectional view of the first outlet channel leading radially inwardly to the first outlet aperture 56, and FIG. 4C shows a cross-sectional view of the second outlet channel 54 as it leads also radially inwardly to the second outlet aperture 58.

Figure 4C:
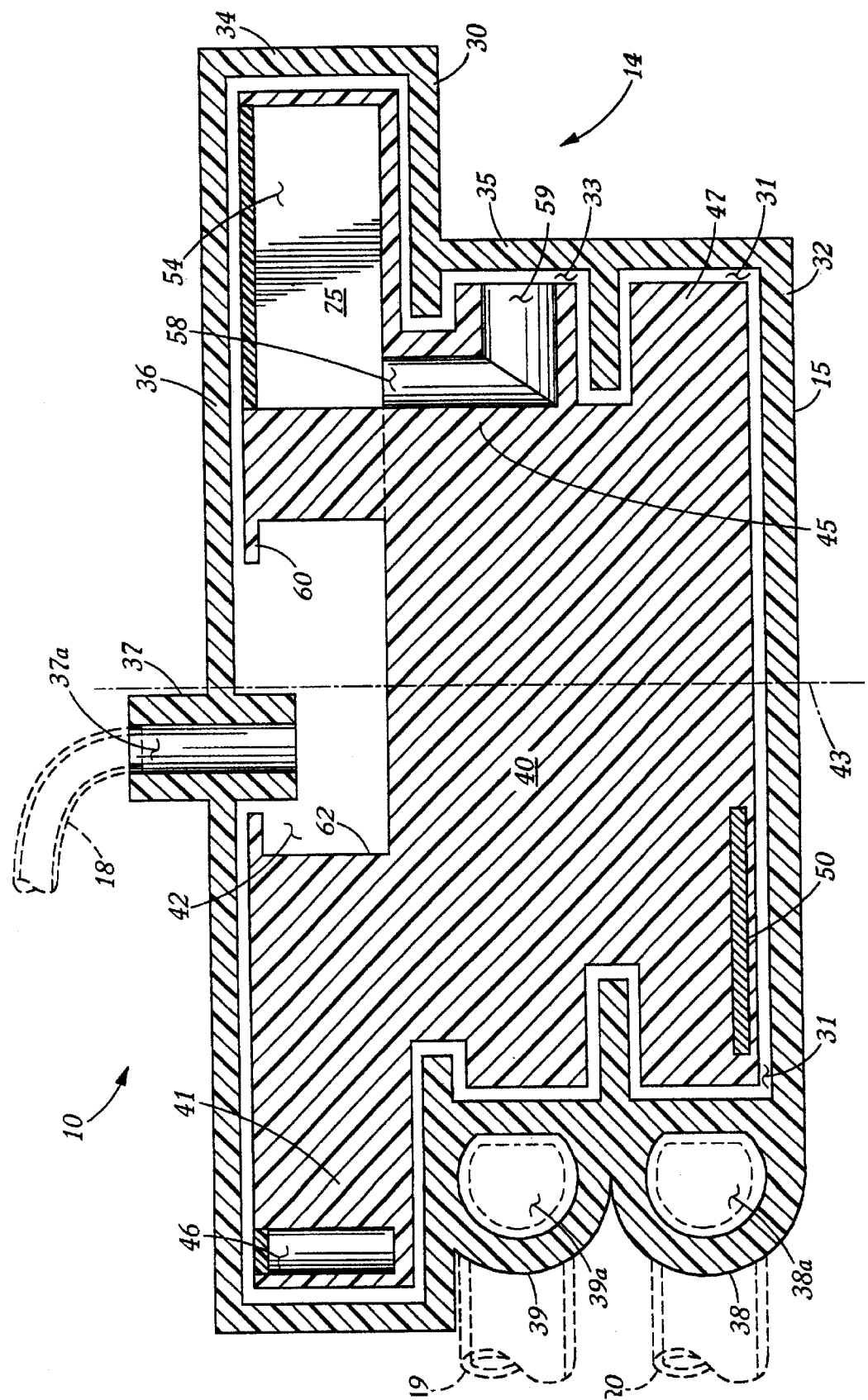

As depicted primarily in FIGS. 3A and 3B, as well as in the various cross-sections of FIGS. 4A–4C, the respective inlet receiving area 42 and channels 44, 46, 52 and 54 are preferably defined by substantially vertical walls, such as the peripheral wall 62 which defines the receiving area 42, the radial walls 64, 65 which define the radial transport channel 44, the respective inner and outer, substantially circumferential walls 66, 67 defining the circumferential channel 46, first outlet channel walls 72, 73 defining the first outlet channel 52 and the second outlet channel walls 74, 75 which define the second outlet channel 54. A portion of wall 74 in the area where it is opposed to outer circumferential wall 67, taken together with that opposed portion of wall 67, define the preferably short continuation portion 46a of circumferential channel 46 as located between the two outlet channels 52 and 54. Generally, adjacent walls are preferably coterminous with each other and may thus meet at corner edges, such as the corner edge 76 disposed between adjacent walls 64 and 66 at the intersection of radial channel 44 with circumferential channel 46. Otherwise, adjacent walls may more preferably merely blend into each other or meet in a graduated merging fashion such as that shown for the meeting of inner circumferential wall 66 with the first outlet channel wall 72 as they lead into and eventually define the first outlet channel No identifiable border need exist here between. A substantially common floor 70 may also define the bottom boundaries of the inlet area 42 and the respective channels 44, 46, 46a, 52 and 54.

An overhanging lip or ledge 60 is preferably also disposed in and around the inlet fluid receiving area 42 to retain fluids within area 42 as will be described further below. This feature is best shown in FIG. 3C, but is also depicted in FIGS. 2, 3A, 3B and 4A–4C. Overhanging lips of this sort may also be disposed on or over other walls covering other fluid passageways or channels (not shown) as may be desired. Further descriptions of such alternatives will become more apparent below. As another alternative, a covering ceiling (not shown in FIGS. 1–5; but see FIGS. 6 and 7A, 7B) can be attached over the respective channels and/or a substantial portion of the inlet receiving area to retain the fluids there within. An example of such a ceiling is shown and described with respect to the alternative embodiment of FIGS. 6 and 7A, 7B which include a ceiling 80 therein, see below.

Returning now to FIG. 1A, a general description of the preferred blood and blood component flow paths, when device 10 is used for the separation of blood into components, will now be described. First, as shown here, whole blood is drawn from the donor 11 (or other source, e.g., a bag of blood) and flows through tubing line 18 to the top of the centrifuge device 14. If as shown in FIG. 1A, and as preferred, no pump is used along line 18, then tubing line 18 will be connected to the top of device 14 in a sealed but, preferably non-rotating seal fashion. Briefly, also shown in this FIG. 1A depiction, are the other tubing lines 19, 20 of tubing system 16 which display the exit flows from the centrifuge device 14 of the separated blood components; namely, red blood cells (RBCs) flowing through tubing line 19 for collection in container 22, and plasma flowing through tubing line 20 for collection in container The alternative tubing line flow paths shown in dashed lines in FIG. 1A and solid and dashed lines in FIG. 1B will be discussed below. Other alternatives such as drawing the composite fluid, like blood, from a non-live donor, i.e., from some other fluid reservoir, will also be discussed below.

Turning to FIGS. 2–5 (primarily FIGS. 3A, 3B and 5), the flows in and through the centrifuge unit 14 of the separation device 10 will now be described. Whole blood from the donor 11 flows from the tubing line 18 down into the centrifuge unit 14 through the inlet aperture 37 defined in the top wall 36 of centrifuge unit 14 and is initially received in the fluid receiving area 42 of the separation layer 41 of the rotor 40. While in the receiving area 42, the blood is exposed to centrifugal forces when rotor 40 is spinning (which the rotor 40 is preferably doing at all times when blood is being introduced into or is otherwise resident within centrifuge unit 14). Note, the initial exposure of blood to the centrifugal forces is enhanced if the inlet aperture 37 is eccentrically disposed relative to the axis of rotation 43 (see FIGS. 2 and 3A where axis 43 is shown as a dot-dash line, and see FIGS. 3B and 5 where it is shown as a crosshead indicating the perpendicularity thereof relative to the drawing sheets of FIGS. 3B and 5). Under the centrifugal forces of the spinning rotor 40, the blood is moved to the periphery of the receiving area 42 and is thus generally moved into contact with the wall 62 which defines the receiving area 42. As can then be seen from FIG. 3C, the whole blood (identified generally therein by the reference number 100) is preferably held vertically within the receiving area 42 by the overhanging lip 60. The blood 100 may also take on a quasi-parabolic shape under a lip such as is shown in FIG. 3C when subjected to the centrifugal forces of a spinning rotor 40.

Figure 5:
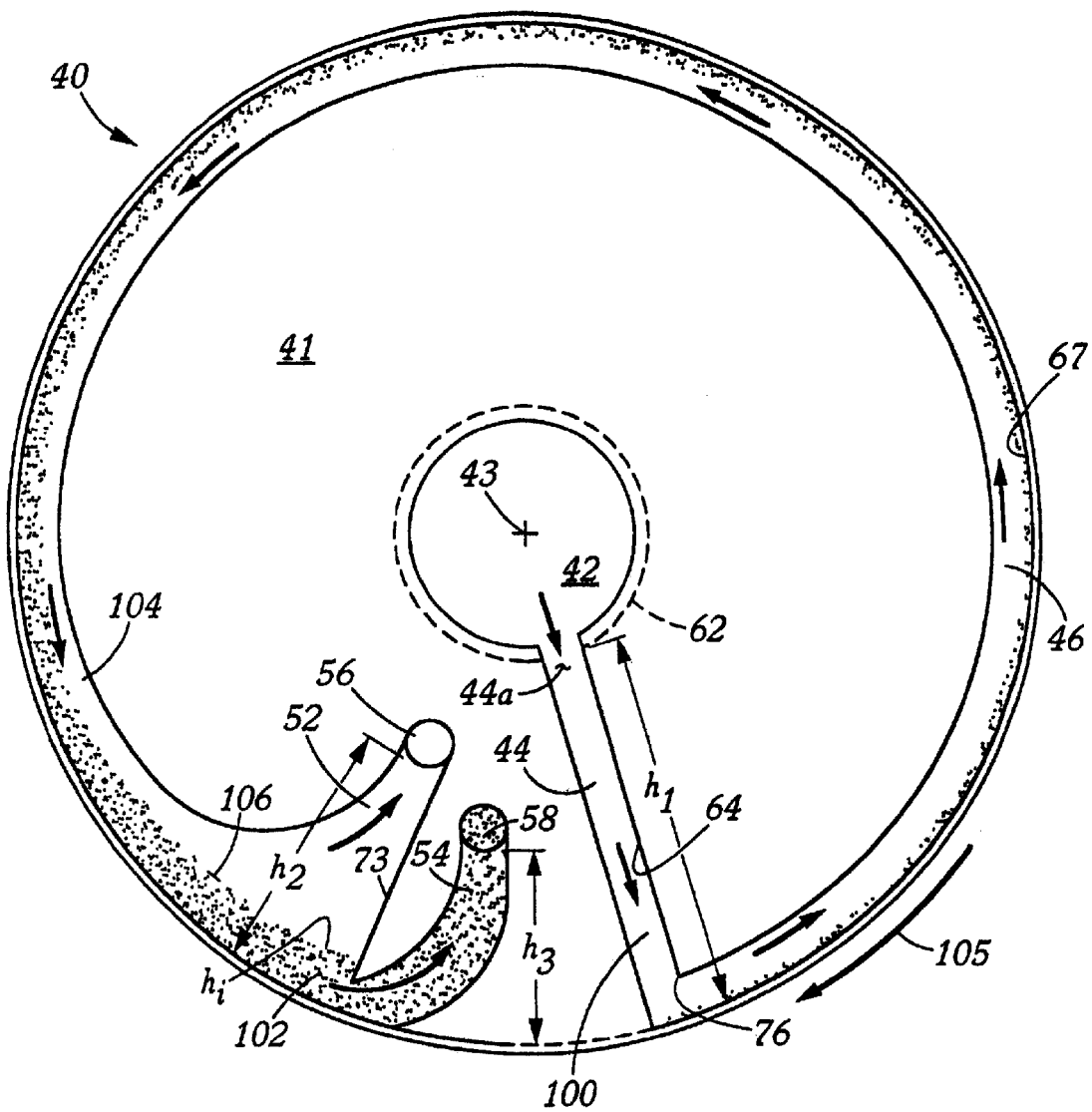
FIG. 5 is another plan view like that of FIG. 3B of a separation layer of a centrifuge unit of a separation device such as that shown in FIG. 3A.

As shown in FIGS. 3A–3C and FIG. 5, a continuous flow of the whole blood 100 will then escape from the fluid receiving area 42 into the radial channel 44. This blood will then travel radially outwardly toward and then flow into the circumferential channel 46. Flow arrows are provided in FIG. 5 to show the direction of flow throughout the preferred centrifugation configuration therein. This flow then continues on around the circumferential channel 46 for ultimate passage out of the separation layer 41 through the outlet apertures 56 and 58. First, it should be noted that when the centrifuge rotor 40 is spinning (again, as it preferably will be whenever blood is disposed therein), this will impart centrifugal forces on the blood which will then separate into at least two primary components; namely, red blood cells (RBCs) and plasma. The heavier phase RBCs will settle outwardly under these centrifugal forces, and will thus accumulate, in a still continuously circumferentially flowing fashion, against or adjacent outer wall 67 of channel 46. This action is shown in detail in FIG. 5, wherein both the radial and the circumferential flows are indicated with arrowheads in the respective channels 44, 46, 52, and 54. The RBCs are identified generally by the reference number 102 in FIG. 5, and the plasma is similarly identified generally by the reference number Also, it should be noted that component separation will likely generally occur, as shown in FIG. 5, throughout the travel of the blood around the circumference of the separation layer 41 within the circumferential channel 46. For this reason, the circumferential channel 46 may also be referred to as the separation channel. Moreover, a generally counterclockwise flow pattern shown by the arrows within the channel 46 in FIG. 5 is shown however, this is not intended to be limiting as clockwise flows are also foreseeably operable. Similarly, a clockwise rotation of the rotor 40 as indicated by the large arrow 105 in both FIGS. 3B and 5 is also shown, particularly in combination with a counterclockwise flow pattern of the fluid in and through the rotor 40 (as described above), although rotation in the opposite direction is again foreseeable with or without a counterclockwise flow in rotor 40.

Even though the flow in and through the circumferential channel 46 is where a substantial part of the separation takes place such that the RBCs are forced toward the outside wall 67 (see FIG. 5), the fluid flow (as well as the fluid separation) is nevertheless preferably continuous throughout. In other words, the inlet flow of whole blood is preferably continuous as are the outlet flows of plasma and RBCs. This flow continuity is preferably driven by the relative off-set "heights" of the inlet and outlet ports 44a, and 58 as will now be described in more detail. The term "heights" is used here in a fluid static, dynamic, and/or fluid pressure-balance sense for referring to various fluid distances measured from a common though generally arbitrary baseline such as the outer fluid flow separation channel circumference of the centrifuge separation layer 41 radially inwardly toward the axial center 43. However, though the inlet and/or outlet positions or "heights" are measured on a radial, each such channel need not be in a radial disposition. Circuitous flow channels not adhering to radial dispositions are available within these relationships as well. More specifically, the height of the radial transport inlet port 44a of channel 44 is the height, or represents the relative radial position of the inlet port 44a of the channel 44, also designated as $_1$ in FIGS. 3B and 5 from the peripheral channel wall 67 to the inlet port 44a. The outlet port heights are similarly the relative lengths or represent the relative radial outlet positions of the outlet flow channels 52, 54 and are designated $h_2$ and $h_3$, respectively in those same FIGS. 3B and 5. Then, for a fluid to be able and/or driven to flow from the inlet toward the outlets, the inlet fluid static pressure, $\rho_1 g_1 h_1$, in the transport channel 44 must be greater than either of, or in some embodiments, at least the larger of the two outlet fluid static pressures, $\rho_2 g_2 h_2$ and $\rho_3 g_3 h_3$. ($\rho_{(1\ 23)}$ is the fluid density, $g_{(1,\ 23)}$ is the gravitational or centrifugal acceleration quantity and $_{(1,\ 2}$ is the relative fluid height of each channel as described above). Thus, for the preferred positive flow in the direction of the arrows in FIG. 5;

$$\rho_1 g_1 h_1 > \rho_2 g_2 h_2 \text{ or } \rho h_1 g_1 h_1 > \rho_3 g_3 h_3 \qquad \text{(Equation 1)}.$$

Furthermore, though accurate as a generalized concept, this summarization is both subject to simplification and/or may in other ways be somewhat over-simplified. The primary invention selectable driving values are the respective h quantities as have been distinctly defined above. However, even though the respective g gravitational acceleration values are more purely non-constant variables (as depicted by the subscripts 1, 2 and 3 therein), particularly in view of the large centrifugal forces applied in the present system and the different radial lengths of each column, these may be nevertheless considered substantially similar values. Moreover, particularly when considering the driving variable relationships herein under practical consequences (the h's and ρ's will vary more widely); the g values may be considered as substantially equivalent values throughout the above equation for each of the above pressure values (at least when operating within a substantially common centrifugal force field as well as the common gravitational field presented in a single latitude and altitude relative to the earth). In other words, the differences between the different g values are small enough such that the selection of the respective h values will accommodate them in the desired centrifugation configuration. Similarly, though the ρ will likely provide greater distinctive differences for each term in this formula, the relative h values may be chosen to accommodate for these also. Note however, these ρ are dependent on the fluids flowing herein and are not as amenable for selecting or for establishing the desired configuration. In blood separation, the first ρ value, in $\rho_1 g_1 h_1$, is the density of the fluid in the transport channel 44; here of whole blood before separation, whereas, the second and third ρ values, appearing in $\rho_2 g_2 h_2$ and $\rho_3 g_3 h_3$, represent the respective densities of the fluids in the two outlet channels 52, 54; here of the separated blood components, plasma and RBCs. Moreover, the second ρ value, in $\rho_2 g_2 h_2$, includes both a plasma and an RBC component, such that the pressure term $\rho_2 g_2 h_2$ is actually the sum of an $\rho_{RBC} g_{RBC} h_i$ value and an $\rho_{plasma} g_{plasma}(h_2 - h_i)$ value. The $h_i$ value is shown in FIG. 5 as the height of the interface of the separated RBCs 102 with respect to the separated plasma 104 in or adjacent the outlet channel The interface between the RBCs and plasma is identified by the general reference number 106 in FIG. 5. Thus, the hydraulic pressure term for the plasma outlet channel 52 is the sum of the above interface related values as in $\rho_2 g_2 h_2 = \rho_{RBC} g_{RBC} h_i + \rho_{plasma} g_{plasma}(h_2 - h_i)$. The terms for use in the selection of respective heights for creating the preferred positive direction flow according to Equation 1 are thus defined. Still further, it is the location of the interface 106 between the RBCs and the plasma which is, according to the present invention, sought to be controlled such that the height, $h_i$, thereof remains within a certain preferred range as the interface 106 meets with wall 72 of the plasma outlet 52. This height, $h_i$, of interface 106 will thus preferably be so maintained by the pre-selection of the respective heights $h_2$ and $h_3$ so that they are related to each other such that the fluid pressure values of $\rho_2 g_2 h_2$ and $\rho_3 g_3 h_3$ (as generally introduced relative to Equation 1, above) are equal to each other, i.e., $$\rho_2 g_2 h_2 = \rho_3 g_3 h_3 \qquad \text{(Equation 2)}.$$

This then provides a hydraulic or hydrostatic pressure balance to maintain the interface at a substantially static height. But note here also, the ρ value in this $\rho_2 g_2 h_2$ has both an RBC and a plasma component such that $\rho_2 g_2 h_2$ is again the sum of a $\rho_{RBC} g_{RBC} h_i$ and a $\rho_{plasma} g_{plasma}(h_2 - h_i)(h_i$ again being the height of the interface, as shown in FIG. 5). And, Equation 2 becomes more particularly, $$\rho_2 g_2 h_2 = \rho_{RBC} g_{RBC} h_i + \rho_{plasma} g_{plasma}(h_2 - h_i)$$
$$= \rho_{RBC} g_{RBC} h_3 = \rho_3 g_3 h_3 \qquad \text{(Equation 3)}.$$

Moreover, the fluid pressure terms ρgh may be more accurately be considered as summations (e.g., $\Sigma(\rho g h)_n$) of contributing parts whether of unit parts of the length (e.g., where the density of a constant fluid may exhibit variation along the length or height of a column; summation or even integration may be used herewith) or when perhaps multiple fluids more accurately contribute to the pressure in a given column. As a first example, the first ρ value, in $\rho_1 g_1 h_1$, may include both a whole blood and an RBC component, such that the pressure term $\rho_1 g_1 h_1$ may actually be the sum ($\Sigma(\rho g h)_1$) of an $\rho_{RBC} g_{RBC} h_i$ value and an $\rho_{whole\ blood} g_{wholeblood}(h_1 - h_i)$ value. The $h_i$ value is shown in FIG. 5 as the height of the interface 106 of the separated RBCs 102 with respect to the separated plasma 104 in the peripheral channel 50. Thus, the hydraulic pressure term for the inlet channel 44 may be the sum of the above interface related values as in $$\rho_1 g_1 h_1 = \rho_{RBC} g_{RBC} h_i + \rho_{wholeblood} g_{wholeblood}(h_1 - h_i).$$

The terms for use in the selection of the respective heights for creating the preferred positive direction flow according to Equation 1 may thus be more fully defined. For example, Equation 1 can approach:

$$\Sigma(\rho g h)_1 > \Sigma(\rho g h)_2, \text{ or, } \Sigma(\rho g h)_1 > \Sigma(\rho g h)_3.$$

Similarly, the second ρ value, in $\rho_2 g_2 h_2$, includes at least a plasma and usually also an RBC component, such that the pressure term $\rho_2 g_2 h_2$ is actually the sum ($\Sigma(\rho g h)_2$) of an $\rho_{RBC} g_{RBC} h_i$ value and an $\rho_{plasma} g_{plasma}(h_2 - h_i)$ value. Thus, the hydraulic pressure term for the outlet channel 52 is the sum of the above interface related values as in $$\rho_2 g_2 h_2 = \rho_{RBC} g_{RBC} h_i + \rho_{plasma} g_{plasma}(h_2 - h_i).$$

Note, the $\rho_3 g_3 h_3$ pressure term in these equations could also be thought of in composite parts; however, as shown and described it will generally have only one component fluid (the heavier phase separated component) and thus may be thought of more generally (for example using an average g value and an average ρ value to arrive at a single ρg value such as $\rho_{RBC} g_{RBC}$ for separated RBCs.

Note, in the preferred situation where $\rho_1 g_1 h_1 > \rho_2 g_2 h_2$ or $\rho_3 g_3 h_3$ and where $\rho_2 g_2 h_2 = \rho_3 g_3 h_3$, the flow dynamics here will be such that in any event where any part of any term changes, the selected relationship will bring the pressure terms as a whole back or automatically readjust to equalization. Thus, if for some reason $\rho_3$ were to change (e.g., become lesser or greater) during operation, then flows will change such that the interface $h_i$ will move to counteract this change. In an example if the $\rho_3$ were to become greater such that the $\rho_2 g_2 h_2$ term would tend to grow in value, then the $\rho_3 g_3 h_3$ term would tend to grow, likely by flowing faster (or likely at least not at its previous rate) and gain by raising the interface, e.g., the $h_i$ term in the previously established relationship: $\rho_2 g_2 h_2 = \rho_{RBC} g_{RBC} h_i + \rho_{plasma} g_{plasma} (h_2 - h_i)$. As another example, if the less dense component (e.g., plasma) lessens at any time, it will get preferential flow out of one port (e.g., the plasma port), and the heavier component (e.g., RBCs) will slow or not flow until the $\rho_2 g_2 h_2$ term increases as described above, e.g., when the $h_i$ term rises sufficiently. Moreover, all three columns will go toward equalization in a no-flow situation (e.g., the $h_1$ will drop to a level (particularly if no further fluid supplies the inlet channel 44) such $\rho_1 g_1 h_1 = \rho_2 g_2 h_2 = \rho_3 g_3 h_3$; at which point flow will be stopped. This provides an automatic flow stop or shutoff feature when supply of composite fluid in containment area 42 is extinguished (the heights will then generally assume a relationship such as $h_2 > h_1 > h_3$). In any event, these relationships will tend to drive toward an equalization, even if flow in one or more of the columns stops for a period; and the terms may not always be equal, but they will equalize.

In all of these cases then, the configuration selectable values are preferably the h values. The particular fluids to be and consequently separated dictate the ρ values, and the g values are governed mainly by the centrifugal forces applied to the system. Thus, when deciding the size and relative configuration of the desired centrifugation system, the selectable values are the inlet channel length $h_1$ relative to outlet channel lengths $h_2$ and $h_3$; as well as the relative outlet lengths $h_2$ and $h_3$ to each other according to the above Equations 1, 2 and 3.

Control over interface 106 using Equations 2 and 3 provides a distinct advantage. First, if interface 106 were not so controlled, it could fall either radially outwardly below the extent of wall 73 such that separated plasma would spill into the RBC outlet channel 54 and undesirably dilute the RBC product flowing out outlet 58. Or, the interface 106 could alternatively, ride too high, radially inwardly, along wall 73 such that a buffy coat component and/or RBCs could spill into the plasma outlet 56. The "buffy coat" blood component, as known in the art, generally rides on the interface 106. The buffy coat generally includes platelets and white blood cells therein. And, if the interface 106 is not controlled or maintained a sufficient distance from either of the outlets 56, 58, then these buffy coat blood components could spill into and contaminate either of the RBC or plasma products. White blood cells (WBCs) are particularly unwanted in both RBC and plasma products due to the possible contamination of such white blood cells with certain undesirable pathogens, including HIV viral contamination, for example. However, because centrifugal separation will less effectively separate WBCs from RBCs, the WBCs are more likely to be addressed separately relative to the RBCs with a post-centrifugal filtration. In other words, the present invention, like other centrifugal separation systems, will most likely not sufficiently leukoreduce red blood cells. Rather, although the buffy coat including the WBCs will preferably ride on the RBC layer, they will not likely be sufficiently separated from the RBCs here so as to produce a leukoreduced RBC product. However, the buffy coat including WBCs can be sufficiently centrifugally separated from the plasma product by the present invention so long as the height of the interface $h_i$ is sufficiently controlled as taught herein.

Nonetheless, once the whole blood 100 has traveled through the separation channel 46 and has been separated into components, particularly into RBCs 102 and plasma 104, then these components 102 and 104 will flow out through their respective outlets, namely outlets 58 and 56. Again, as this is a continuous flow process, the whole blood 100 continuously flows into the centrifugal configuration, particularly the separation portion 41 of centrifuge unit 14, and blood components 102 and 104 are continuously separated therein and continuously flow out of the centrifugal configuration separation portion 41 of centrifuge unit 14 through the outlets 58 and Then, for the further description of the flow process from these outlets forward, reference is turned again to FIGS. 4B and 4C which show one preferred embodiment providing for the collection of the separated blood components from the separation layer outlets 56 and moving or otherwise allowing for the movement of these components out of the centrifuge unit 14 and separation device 10.

Specifically, FIG. 4B shows an embodiment wherein the plasma outlet 56 leads to an exit passageway 57, which, in this embodiment, first extends substantially vertically downwardly through the rotor 40 until it reaches the lower layer 47, and then it extends radially outwardly to and through the exterior surface of the lower layer 47 of the rotor 40. This substantially L-shaped passageway 57 thus provides fluid communication from the outlet 56 to the lower interior circumferential channel 31 of the housing 30. In this way then, fluid passing through outlet 56 then flows through passageway 57 and then empties from the rotor 40 into the rotor housing 30 within the lower channel 31 thereof. Lower channel 31 is then also in fluid flow communication with the outlet 38 which thereby allows for fluid flow out of housing channel 31 into and through outlet 38, and from there, into and through tubing line 20 ultimately up to fluid container 24 (see Fig. Note, in the embodiment shown here, the fluid preferably retains an amount of kinetic energy imparted thereto by the spinning centrifuge, and this kinetic energy may be effectively converted into a fluid flow pressure which can force a non-centrifugal flow of the fluid in and through the tubing line 20, and a further flow even upwards, against the pull of gravity, into a hanging storage bag 24. The components involved in causing this action; particularly the lower layer 47 of the rotor 40, and the channel 31 of the housing 30, may thus be referred to as a pump of a centrifugal or vortex type. Note, bag 24 need not be hung above separation device 10, but may be hung on a level with or even below device 10. The quantity of kinetic energy thus required (if any) to be maintained can thus be a function of such receptacle location as well as the length of travel thereto, among others.

Similarly, as shown in FIG. 4C, the RBC outlet 58 leads to an exit passageway 59, which in the embodiment shown here, first extends downwardly through the rotor 40 until it reaches the intermediate rotor layer 45, and then it extends radially outwardly to and through the exterior surface of the rotor layer 45. Thus, as above, this RBC passageway 59 provides fluid communication from the RBC outlet 58 to an intermediate interior circumferential channel 33 of the housing 30. Fluid then passing through outlet 58 flows through passageway 59 and then empties from the rotor 40 into the intermediate channel 33 within the rotor housing 30. Channel 33 is then also in fluid flow communication with the RBC outlet 39 thus allowing for fluid flow out of channel 33 into and through outlet 39, and from there, into and through tubing line 19 ultimately up to fluid container 22 (again, see FIG. 1A). Moreover, as was true above, the fluid reaching the interior channel 33 preferably retains an amount of kinetic energy imparted thereto by the spinning centrifuge, and this kinetic energy may here also be effectively converted into a fluid flow pressure which can cause or force a non-centrifugal flow of the fluid in and through the tubing line 19, and even up, against the pull of gravity, into a hanging storage bag 22. The components here too involved in causing this type of action; particularly the intermediate layer 45 of the rotor 40, and the channel 33 of the housing 30, may thus also be referred to as a centrifugal or vortex type of pump. Here also, bag 22 need not be above device 10 but could be on a level with or even disposed there below. The amount of kinetic energy thus required (again, if any) can thus be dependent on such receptacle disposition and the relative distance therefrom, among others.

Several important advantages are achieved with a device such as that shown and described herein. A first such advantage is the elimination of numerous control elements which were often required in previous centrifugal separation systems. For example, the hydraulic pressure-balanced interface controls shown and described here eliminate the need for optical or other feedback loop interface control elements. The present pressure-balance controls are also substantially independent of the blood hematocrit and relative flow rates of the inlet and outlet fluids. This eliminates the need for complex flow rate calculations and pump controls therefor (i.e., eliminates computer calculations and multiple flow control pumps; in various conventional embodiments, multiple pumps, inlet and outlet, have been required to be maintained in dynamic control relationship with each other constantly by computer in order to provide proper interface control). Thus, at the least, no inflow pump is required here, and blood may instead be gravity drained/fed into this separation device. The lack of an inflow pump and use of a magnetic or an otherwise non-contact drive mechanism further eliminates the need for a rotating tubing loop. This serves to greatly reduce the quantities and sizes of the mechanical components (tubing loops in rotating loop systems generally dictate the minimum mechanical element requirements and size), and thus also allows for an overall reduction in scale of the separation device as a whole. A gravity feed system (no inflow pump) also eliminates any need for a rotating seal at the inlet connection of the inflow line to the separation device. This greatly reduces complexity and a large potential for operational failure. Also, the rotor and housing combination are easily made in a totally closed system which can be simply sterilized and can be completely disposable, particularly if non-invasively driven by a rotational magnetic motor as described herein. The reduced scale and mechanical complexity contribute to the disposability benefits as well.

A further advantage can be realized in the output product quality. In particular, a virtually constant maximum hematocrit may be obtained for all resultant red blood cell products because the presently described separation device may be operated within a range of revolutions per minute (RPMs) at which the product hematocrit does not substantially vary. For example, the present invention may be operated at high speeds of a few to many thousands of RPMs, speeds which are heretofore not achievable for various reasons (e.g., drive mechanism or rotating seal problems at such high speeds). And, at such speeds, virtually all RBCs will be separated out from the input whole blood, thus yielding an RBC product with the highest available hematocrit. Note, the highest available hematocrit is a number above 80% and less than 100% and which approaches a substantially constant asymptote which is in the area of approximately 90 or 95%. At speeds in the range of high RPMs, the resulting hematocrit is virtually equivalent to the asymptotic maximum throughout that range. At much lower speeds (e.g., below 3000 RPMs), the resulting hematocrit may significantly diverge from the asymptotic maximum.

Referring once again to FIGS. 1A and 1B, a few basic alternatives will now be addressed. First, the use of an anticoagulant (AC) may be preferred and particularly is preferred when a direct connection to a donor 11 is made as shown in FIGS. 1A and 1B. Note, the present invention may be used in a process (not shown) to separate previously collected composite fluids, like blood, without the need for anticoagulant addition (in the case of previously collected blood; such blood will very likely already have an anticoagulant added thereto, and thus does not require additional quantities thereof). Thus, an anticoagulant container 110 is shown in dashed lines in FIG. 1A, and in solid lines in FIG. 1B, as it might be incorporated into the overall system. In particular, the anticoagulant container 110 may be connected to a tubing line 112 which is in turn connected to a manifold 115 disposed in fluid communication with the blood inlet line 18 (all shown in solid lines in FIG. 1B). Such a manifold connection is known and used frequently in this field of art. The anticoagulant may then be allowed to free-flow into the tubing line 18, such free-flow being controlled by careful selection of the inside diameter of the AC tubing line 112, or additionally and more preferably, an anticoagulant pump 140 (dashed lines in FIG. 1B) may be used to control the inflow of AC into the inlet line 18. Peristaltic pumps for this purpose are well known in this field (as are other pump types; e.g., linear piston plunger pumps, among others). A scale 136 is depicted in FIGS. 1A and 1B to demonstrate one version among a plurality of known alternatives which may be used to ensure accurate AC feeding into the system.

Another basic alternative available with this invention involves the optional return of certain separated blood components back to the donor, rather than retaining these in the collection reservoirs 22, 24. An example embodiment for returning a quantity of either (or both) separated RBCs and/or separated plasma back to the donor 11 is also shown in FIG. 1A in dashed lines and in solid lines in FIG. 1B. In particular, three return tubing lines are shown such that a first such tubing line 120 is connected to an outlet port in RBC bag 22, a second tubing line 122 is similarly connected to an outlet in plasma bag 24, and a third tubing line 124 connects both of return lines 120 and 122 with the manifold 115 described above. A Y-shaped connector 125 may be used to connect lines 122 with line 124. Then, if and/or when during a separation procedure it may be desired to return a quantity of a separated component (RBCs or plasma) to the donor 11, the desired component may then be allowed to flow out of its respective container 22 or 24, through its respective return line 120 or 122, through the Y connector 125, through the common return line 124, into and through manifold 115, then back toward and into the donor 11 through the donor line 18a.

Accomplishment of these particular flows may simply involve gravity drainage of the desired blood component from its collection/storage bag 22 or 24, and/or it may involve the use of one or more pumps, preferably of the peristaltic type, for example, see pump 142, respective to line 124 in FIG. 1B (dashed lines). Thus, respective pumps may be engaged with each return line 122 (not shown) and/or with line 124 (pump 142), and then may be activated at a desired operational point to pump the desired separated blood component out of its reservoir and through the respective tubings, and back into the donor 11. Various clamps or other flow stoppage mechanisms (not shown) may also be used and variously engaged with any one or more of these tubing lines depending upon which fluid component is to be returned or not, as the case may be. For example, if RBCs are to be returned, then a clamp or other flow stopping mechanism may be engaged with the plasma return line 122, as well, for example, as engaging if desired such a flow stopping mechanism on the main tubing line 18 (and on the AC line 112 if such is being used). Then an RBC flow may be established through the RBC return line 120 back to the donor 11. Note, the use of the bags 24 might provide for an air or bubble trapping effect (as is known in the art) prior to return to the donor/patient 11.

Other variations abound. For example, lines 120 and 122 may each reach to the manifold 115, thus eliminating the intermediate return line 124 and Y connector Also, these return lines (with or without an intermediate line 124) may be run to a second needle (not shown) to alleviate concern for altering (e.g., stopping or clamping) flow through main line 18 for periods or modes of blood return. Another example may include the use of an intermediate reservoir (not shown), for example, at the connection of the return lines 122 to the intermediate line 124 (e.g., at the location depicted by, and in lieu of, the Y-connection mechanism 125). Such a reservoir could fulfill several goals, as for example, providing an air or bubble trap (as is known in the art) prior to return of components to the donor/patient 11. This may be a redundancy to bags 22, 24 or could remove air perhaps introduced by such bags 22, 24, or such an intermediate reservoir could provide a sort of holding capacity in a single needle system such that separated components may be accumulated therein until a certain amount is achieved at which point an automatic (or manual) control mechanism could switch on a pump 142 to activate a return cycle for return of the accumulated components to the donor/patient 11. As above, such a switch could also entail a clamping of the inlet flow line 18, or perhaps this inlet flow may remain undisturbed during such a return cycle.

Such an intermediate reservoir might also be useful with a further alternative embodiment shown in dashed lines in FIG. 1B; the use of optional direct tubing connections from the separated component outlets to the donor return lines. See in particular branch connection lines 121 and 122 in FIG. 1B (dashed lines). Note, these connection lines may merely flow back to the donor without being connected to an outlet line from the respective reservoirs. A flow or flows of separated components can thus be diverted back to the donor 11 prior to being accumulated in either respective collection storage bag Such directed flow(s) could then run through the respective return line 120 and/or 122 into and through Y-connector 125 and back to the donor 11. Or, these diverted flows could be captured by the above-described intermediate reservoir (not shown) and accumulated prior to return as described. Further optional features which could be used herewith include the switch valves 152 (shown in dashed lines in FIG. 1B) on the separated component outlet lines 19, 20 and/or coactive also with the branch connecting 121, 123. Switch valve mechanisms 150, 152 can be used to divert flow from the main outlet lines 19, 20 directly back to the donor/patient 11. For example, the switch valve 150 can be used either to close off a branch line connection 121 so that flow continues from line 19 into bag 22 or to close off flow through the upper part 19*a* of RBC outlet line 19 and thereby divert flow through branch line Flow through branch line 121 then connects to return line 120 and from there goes back to the donor/patient 11 through connector 125, line 124 and manifold 115. As above, an intermediate reservoir could catch such a re-directed flow and trap bubbles therefrom and/or hold it until a return cycle is called for. Otherwise, particularly in a two needle set-up, the flow may be substantially continuously directed back to the donor/patient A similar action may be created by the switch valve 152 which may close off a branch line 123 to maintain flow from line 20 to bag 24, or switch valve 152 may be directed to close off the upper part 20*a* of line 20 and thereby open up flow to and through branch connection line 123. Flow through line 123 may then connect with return line 122 and flow from there goes back to the donor/patient 11 through the Y-connector 125 (or the not-shown intermediate reservoir), line 124 and manifold 115 to the donor/patient part 18*a* of line 18 for return of the components to donor/patient 11. Lines 120 and/or 122 may then be preferably disposed clamped closed (not shown) above the branch connections 121 and/or 123 or may simply be not connected to the outlets of bags 22 and/or 24 contrary to the alternative which is shown in FIG. 1B.

Another consideration is that these manipulations, i.e., clamping certain lines and/or initiating certain flows whether by pump or otherwise, may be performed manually by a human operator (albeit with certain instructions and/or following certain hierarchical processes), or may be performed by a control device (not shown), which may interpret certain input and/or sensed conditions and perform the appropriate flow control actions therefor or in response thereto. Thus, if for example, a preferred quantity of a separated component (RBCs or plasma) is collected within a storage receptacle, but the other component has not yet reached its desired yield, then the control device may then divert the continuously accumulating excess back to the donor 11, while and until the other component reaches its target yield so that both components may have been collected to preferred yields. This the control device may accomplish by operation of machine-activated clamps and/or peristaltic pumps at the appropriate points. Scales 134, or other quantity measuring devices (not shown) may optionally be used to determine the quantities of separated components collected in the respective bags 22, 24. The scale derived quantities may then be used by either the human operator or the optional control device to determine which steps for continued collection or return may be desired. An optional scale 136 (as introduced above) or other quantity measuring device may also be used in the optional AC administering system, such that it may, for example, provide feedback to a control device so that the control device may determine how much AC will be/has been delivered and thus whether and to what extent corrective flow measures (e.g., more or less pumping) may be necessary or desired.

Note, as shown and described for the most part throughout this specification, the inlet to centrifugal separation device 10 and the outlets from device 10 have preferably not required external pumping means (the inlet through tubing line 18 is preferably gravity driven; and the outlet flows through tubing lines 19 and 20 preferably were driven by centrifugal energy retained in the fluid as it exited the centrifuge separation layer 41 and/or may also be gravity driven). However, other motive means may be employed for any/either of these flows as well. For a first example, a peristaltic or other fluid pump 144 (dashed lines in FIG. 1B) may be used to draw blood from the donor/patient 11 and feed the blood to the separation device 10. However, it should be noted that such an assist, if providing much of an increase over a gravitational pull, will likely require the additional employment of an inlet seal which is not shown in the drawings. An example of such a seal could be a rotating seal, or it could take other forms and thereby require further mechanical inlet flow control means such as a 1ω–2ω loop (described herein and though viable these alternatives are thus less desirable. Even so, the geometries of the centrifugal configuration as shown in the separation layer 41 and described hereinabove, may still provide attractive advantages even in such more complicated alternatives.

Similarly, though centrifugal forces are preferred for moving the separated components out of device 10, other motive means may be used here as well. As a first example (not shown but introduced above), the collection bags 22, 24 may be disposed lower than the separation device 10 and the separated components may then be gravity-drained thereto from device 10. The left-over kinetic energy from the centrifugal process may or may not be used in an adjunct hereto. Another alternative involves the use of external pumps 146, 148 (dashed lines, FIG. 1B) of preferably peristaltic or other alternative types to move the separated components from device through respective tubing lines 19, 20. Note, such pumps 146, 148 may also provide greater assistance with a few of the other FIG. 1B alternatives described above. For example, they may provide an advantage in using either of the branch connections 121, 123 to divert separated component flow back to the donor 11. A positive force may be desirable and/or even necessary (e.g., when device 10 is disposed lower than donor 11) to move fluids back to the donor Thus, optional pumps 146, 148 may provide a desirable assist to any centrifugal (or vortex) pumping action if used as such, from device 10; or pumps 146, 148 may provide the sole driving force for drawing separated fluids from device 10, moving them through respective tubing lines then through connections 121, 123 and then into and through lines 120, 122 back to the donor 11. Even if an intermediate line 124 and a Y-connector 125 is used, pumps 146, 148 may still provide the motive force for flow therethrough as well. Still further even, if an intermediate reservoir (not shown but described above) is used here, these pumps might yet move fluids there into and therethrough. However, with the use of such a potential intermediate reservoir, a further pump 142 on line would likely be preferred to draw fluids out of the intermediate reservoir and move these back to the donor 11 through line 124, manifold 115 and extension 18a.

Figure 6:
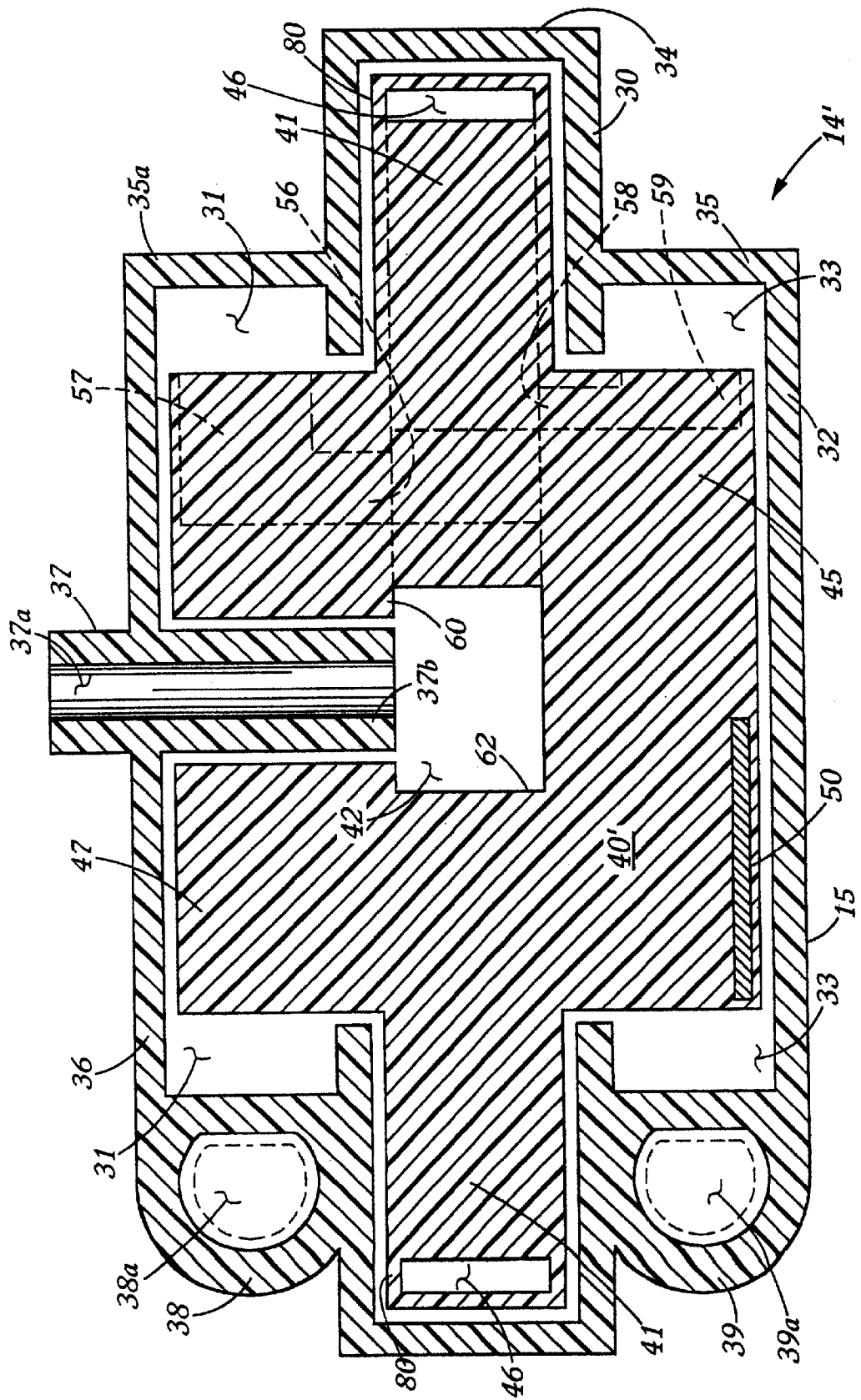
FIG. 6 is a cross-sectional view of an alternative centrifuge unit of a separation device according to the present invention.

Turning now to a few slightly more divergent alternative embodiments, reference is first made to the cross-sectional view shown in FIG. 6. The primary distinction this centrifuge unit" has over that shown, for example, in FIG. 2, is that the separation layer 41 in FIG. 6 has become the intermediate layer of the rotor 40" here as opposed to being the top layer of the rotor 40 as in FIG. 2. The previous lower, plasma collection layer 47 (from FIG. 2) has now been flip-flopped up and disposed on top of the separation layer 41 in this FIG. 6 embodiment, and the previously intermediate RBC layer 45 is now the bottom layer 45. Nonetheless, the functionality remains substantially the same in this embodiment as it was in the FIG. 2 embodiment with the single primary exception that the plasma exits upward out of the separation layer 41 as opposed to downward as in the FIG. 2 embodiment. Further, it is foreseeable that the RBC layer 45 could be disposed on top instead of the plasma layer 47, which could then remain on the bottom, albeit then being adjacent the separation layer 41. Separated components still flow out of separation layer 41 through respective outlet ports 56, 58, and then flow through respective L-shaped channels 57 and 59 to dump into respective circumferential channels 31, 33 of housing 30. Exits out of respective outlet structures 38, 39 are formed also, as before; except that structure 38, is formed within a distinctive upper circumferential wall 35a. Only a few further changes should be addressed. First, the magnetically reactive material is now preferably resident within the RBC layer 45, the new bottom layer in the FIG. 6 embodiment. And, an effective ceiling 80 (as introduced above) is now preferably included over all of the flow channels in the separation layer allowing only an upward exit through the plasma outlet 56. Though perhaps not necessary in a gravity-driven inlet scenario, the downward, inward portion 37b of the inlet aperture structure 37 has been lengthened here to provide continuous inlet fluid guidance until the fluid actually reaches the fluid receiving area 42 of the separation layer 41 of rotor 40". Note, aperture structure 37 is not shown axially off-set as in the previous preferred examples; however, it could be so off-set or not, as desired.

Figure 7A:
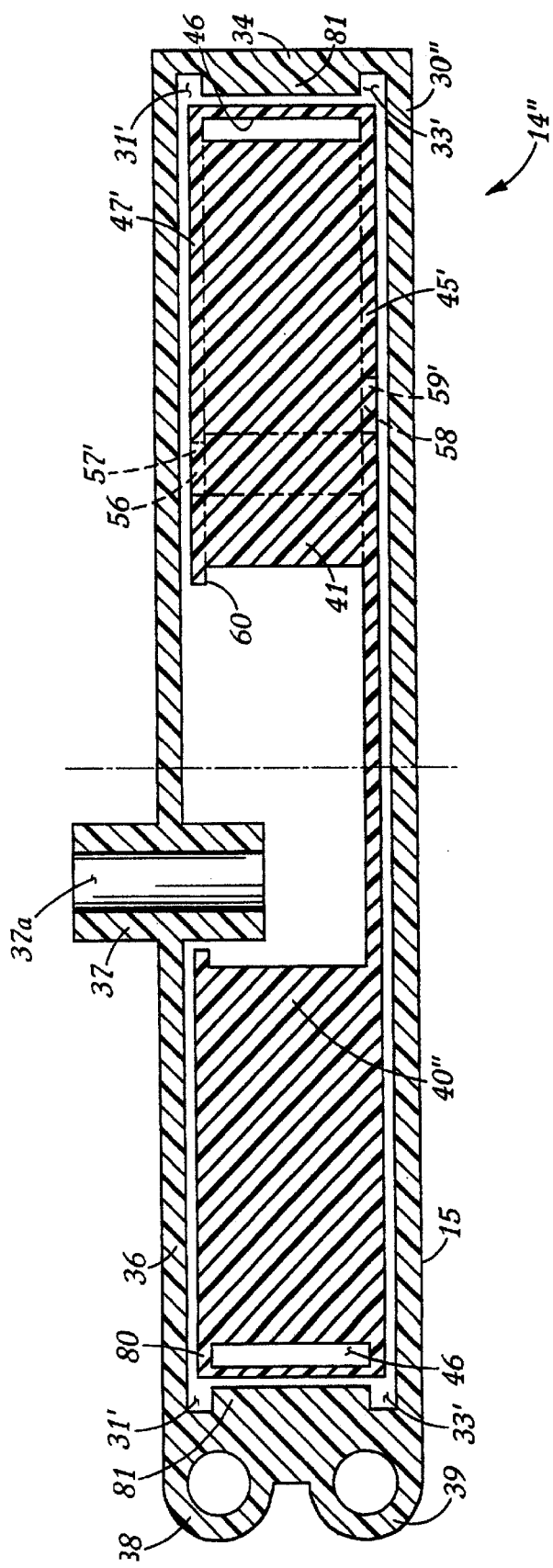

A similar, yet perhaps more simplified alternative embodiment 14" is shown in FIG. 7A. Here also, the separation layer 41 of rotor 40" is intermediate the RBC and plasma layers 45", and 47". However, the exit passages 57", 59" shown in FIG. 3 (in dashed lines) and in detail in FIGS. 4B and 4C have been substantially reduced/removed. In other words, the respective exit ports 56, 58 still provide for exit flow from the separation layer 41 as in the embodiment of Fig. with plasma exiting up through outlet 56 and RBCs exiting down through outlet 58. Only in this FIG. 7A embodiment, the respective outlet passageways 57" and 59" are no longer L-shaped and are extremely short by comparison with the passageways 57, 59 of FIG. 6. Indeed, the FIG. 7A passageway 57", 59" could be considered coincident with and/or extending no further than the outlet ports 56, 58, themselves.

Once separated components exit from the respective ports 56, 58 (and/or passage", 59"), the fluids are outside the rotor 40, but still in the housing 30; in particular, the separated plasma exiting up through port 56 (and passageway 57") is then disposed in a space between the upper housing wall 36 and the top of the rotor 40", this space being designated 31". Space 31" is analogous to the circumferential channel 31 of the FIG. 6 embodiment and is likewise a circumferentially disposed fluid receiving/containing area which then communicates this fluid to the tangentially disposed exit structure 38 for removal of the fluid from the centrifuge 14". A similarly disposed fluid receiving/containing space 33" is established to receive separated fluids exiting port 58 (and passageway 59"), such as RBCs in the primary embodiment.

Note, the embodiment in FIG. 7A includes a ceiling 80 as introduced above, but also preferably includes a circumferential rib or ledge member 81 to help retain fluids disposed in respective receiving spaces 31' and 33'. An extension of the concept behind the ledge 81 of FIG. 7A is shown in more detail in the alternative embodiment shown in FIGS. 7B and 7C. In this embodiment the rotor 40''' has upper and lower circumferential extensions 82 and 84 which extend to greater radial lengths (measured from rotational axis 43) than the centrifugal separation channel 46. The primary advantage is in the heightened definition of the interior receiving channels 31' and 33' so that, as shown in even more detail in FIG. 7C, a separated fluid (RBCs, here) flows out of an outlet port, such as port 58, and then flows radially outwardly (due either to the retained centrifugal energy maintained by the fluid, and/or by action of the still rotating rotor''' to impart centrifugal forces on the exiting fluid with which it is still in contact through the rotor undersurface 85). Then, the fluid is moved, for the most part, into the tangential exit port, here port 39, e.g., however, not all of the fluid will immediately flow into the exit port. Some of the fluid will migrate through channel 33 and seep above extension 84 and move within channel 33' radially inwardly back away from the exit port 39. The advantage here is in the extending of the internal receiving channel 33' by the extension 84 of the rotor 40''' and the consequent ledge adaptation 81' of housing 30''' which accommodates this migratory radial flow. In the circumstances, the rotor 40''' and the extension 84 continue to provide centrifugal forces to the fluid, thus maintaining a positive flow out through exit port 39 as well as establishing a limit on the radial inward creep of the flow above extension 84. This limit may also create a sort of head pressure which also acts to maintain the movement of the fluid radially outwardly to and through the exit port 39.

Also in this alternative arrangement, the pumping action may be referred to as a single-plate Tesla pump which is employed as shown in FIGS. 7B and 7C. The RBC's (or plasma) exit the spinning rotor into a space between the rotor 40''' and stator or housing 30''' where only a small gap (~0.030 inches) is present. The small gap between the bottom surface 85 of rotor 40''' and the housing 30''' ensures that the fluid continues to spin with the rotor 40'''. The exact flow profile of the fluid depends on the specific relative geometry of the rotor and stator. When the fluid spins, large pressures are generated against the stator. An exit port 38 is positioned so that this pressure causes fluid to flow therethrough.

Figure 8:
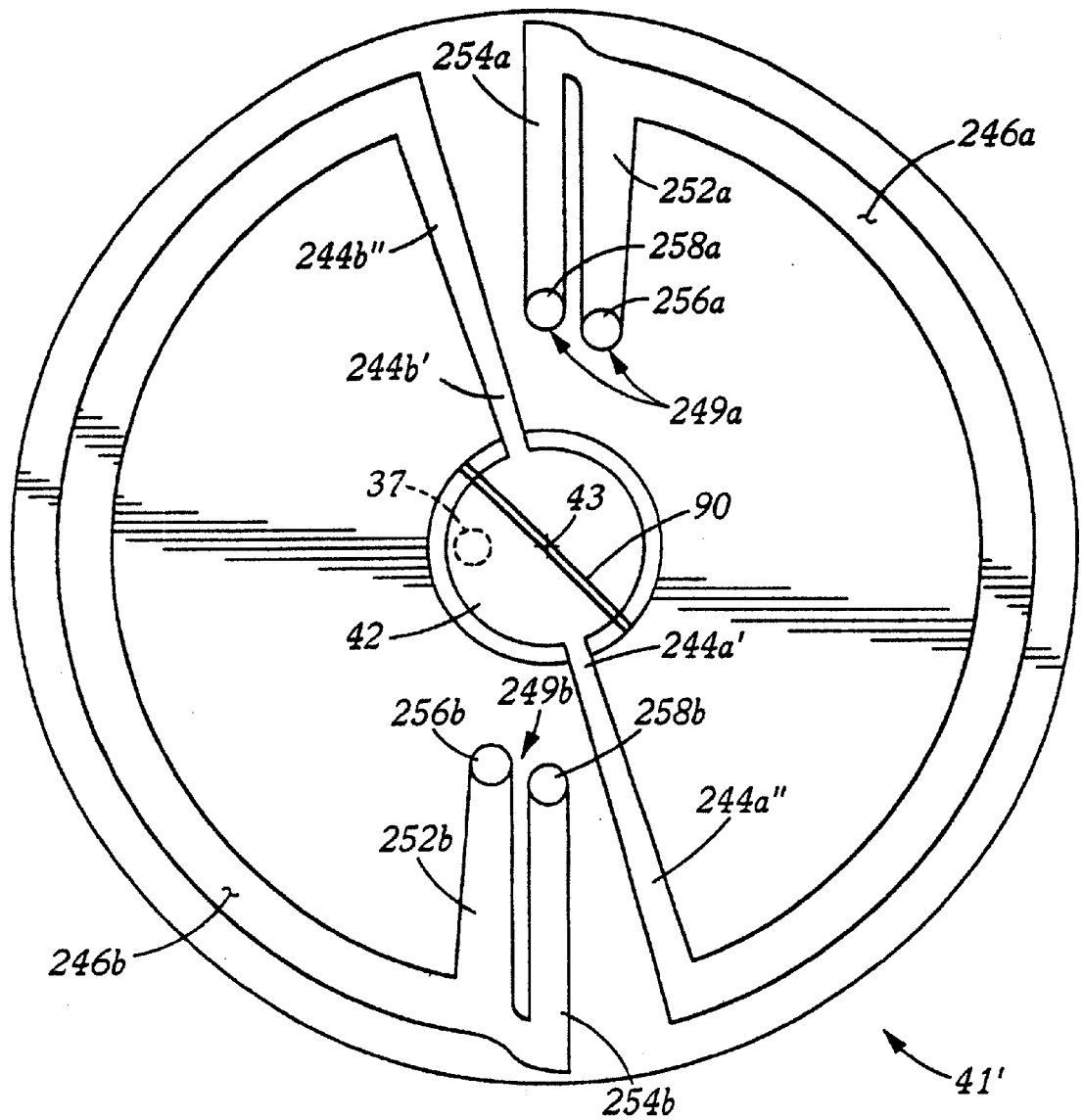
FIG. 8 is a plan view of an alternative separation layer of a centrifuge unit according to the present invention.
Figure 9:
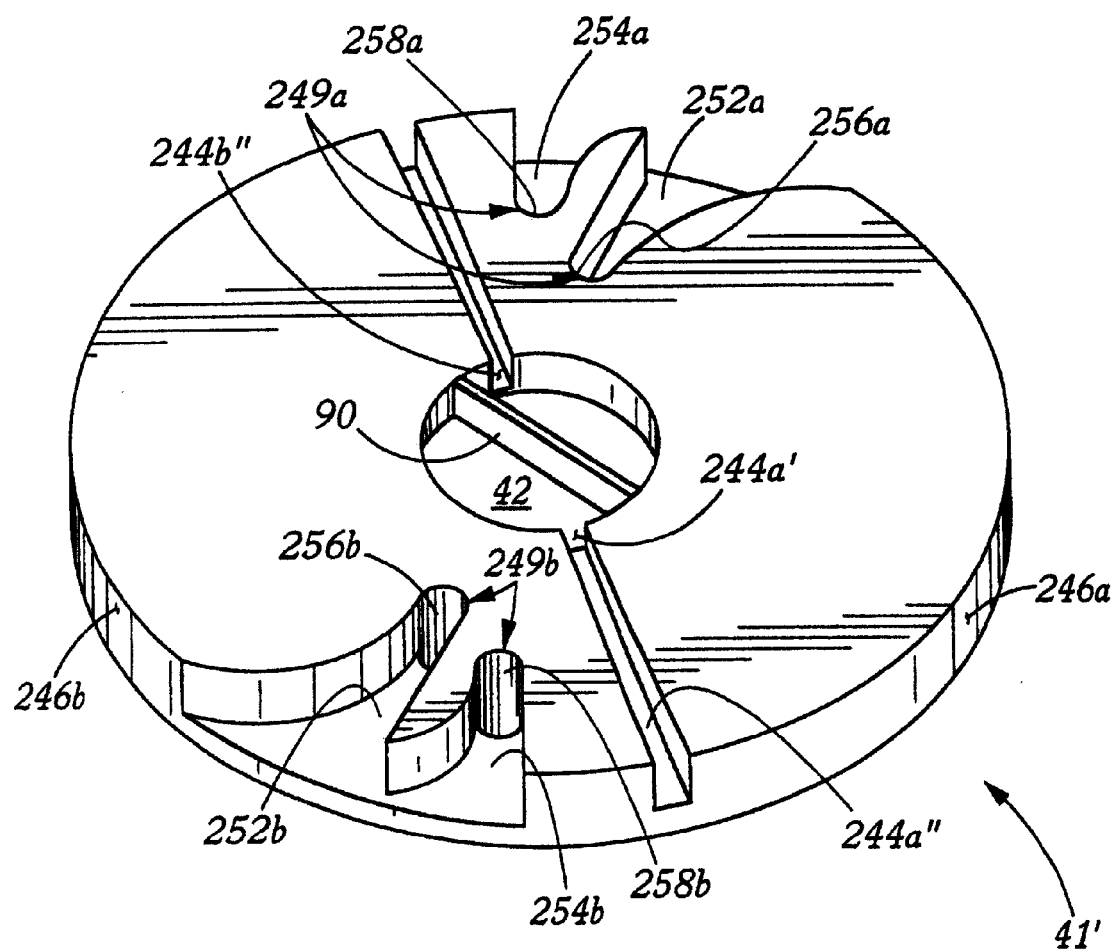
FIG. 9 is an isometric view of the alternative embodiment of the separation device of FIG. 8.

An alternative rotor separation channel scheme is shown in FIGS. 8 and 9. A challenge in implementing the RBC/plasma device described herein involves the rotor weight balance. According to the preferred embodiments, the rotor is spinning when blood enters the system. Thus, a weight balance is preferably maintained whether the rotor is dry or loaded with blood. A first concept that more directly addresses this is shown in FIGS. 8 and 9.

First, the single blood separation pathway 46 of the initially described centrifugation configuration embodiments can be divided into tandem, opposing flow pathways 246*a* and 246*b* as shown in the separation layer 41' of FIGS. 8 and 9. The two flow paths 246*a* and 246*b* balance each other regardless of the material filling the flow paths, whether the materials are air, blood, or any other fluid.

To assist in equally dividing the fluid flow between the two flow paths, blood can be added to the system through port 37 away from the center of rotation (see the axis 43 crosshead on FIG. 8). This alternative was also described above. Thus, the fluid will seek the nearest exit port. The two exit ports 244*a'* and 244*b'* are preferably rotating so during all inflows they will alternate in receiving the inflow from the single entry port 37.

To further encourage equal flow distribution, a septum 90 can be added to the receiving cup The septum 90 preferably extends across the cup 42 and effectively divides it in half with each half having a respective exit port 244*a'* and 244*b'*. Thus, once the fluid enters a particular half of the receiving cup, its exit pathway is guaranteed. Flow then would continue outward through respective radial transport channels 244*a'* and 244*b'*; then into the respective circumferential channels 246*a* and 246*b*. Separation of the composite fluid then continuously occurs and flow continues on around the separation layer 41' simultaneously in the two channels 246*a* and 246*b* to the respective outlet channels 252*a*, 254*a* and 252*b*, 254*b* and from there, as separated fluids, then out of the centrifugal configuration through respective outlet ports 256*a*, 258*a* and 256*b*, 258*b*. From here, the separated fluids would be flowed to respective collection/receiving areas or channels (not shown here), which in one embodiment are like those respective channels 31, 33 of FIGS. 2 and 4A, 4B, 4C (with the primary distinction, of course, of having more than one passageway flowing fluids there into). The other alternative embodiments of FIGS. 6 and 7A, 7B, 7C, among others not shown here, could also be used herewith. More than two tandem channel configurations could also be used to achieve the weight balancing sought here.

Figure 10:
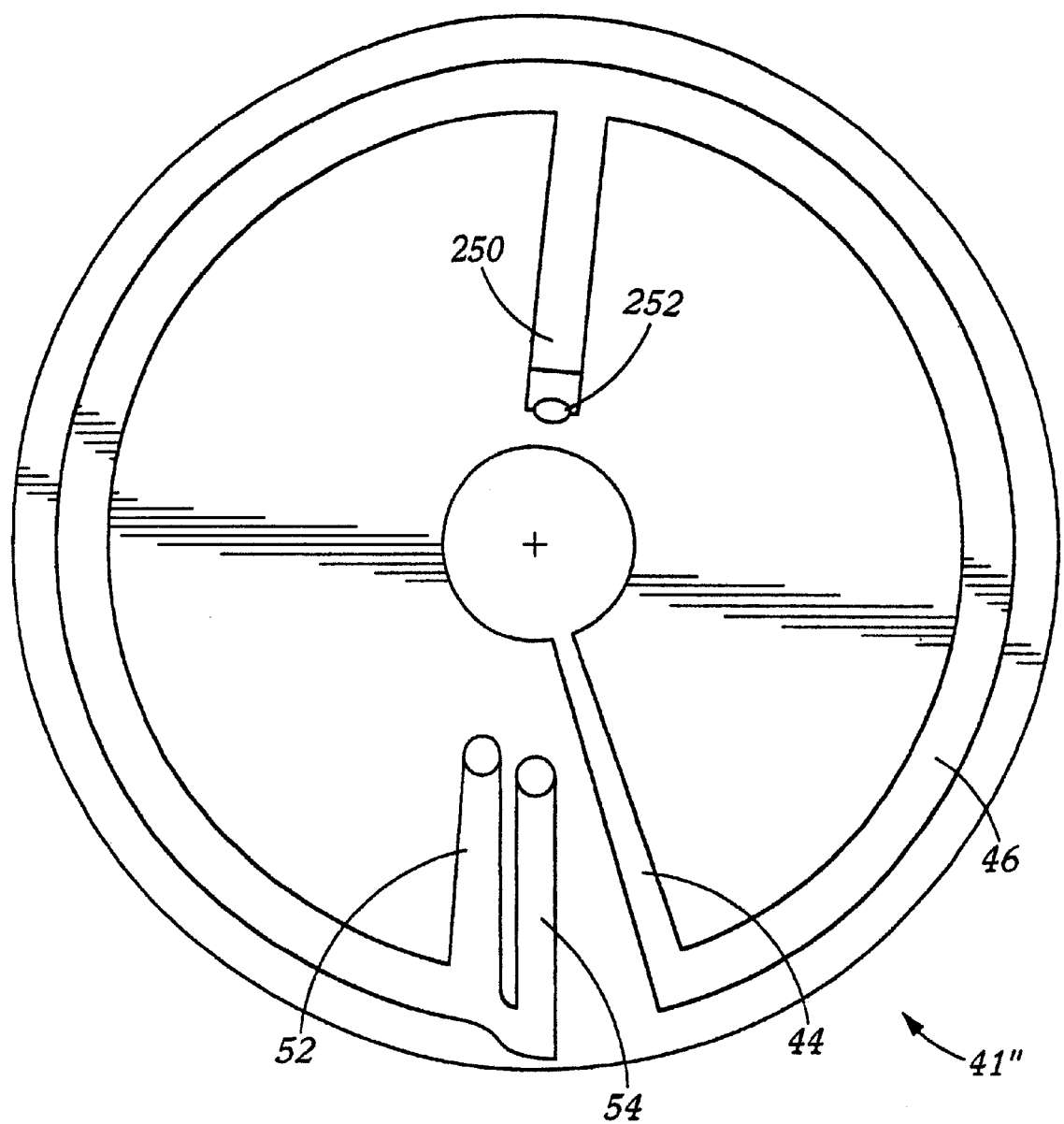
FIG. 10 is a plan view of a further alternative separation layer according to the present invention.

An alternative second concept for a wet/dry weight balance involves a plasma-filled, static column 250 that fills substantially simultaneously with the fluid pathway legs 44, 52, 54, as shown in the separation configuration 41' in FIG. 10. The plasma column 150 has a geometry that counterbalances the whole blood-in leg 44 and plasma-out and RBC-out legs 52 and 54 as they fill. The counter-balance would preferably have a vent hole 252 for air displacement therefrom during initial filling or priming.

Figure 11:
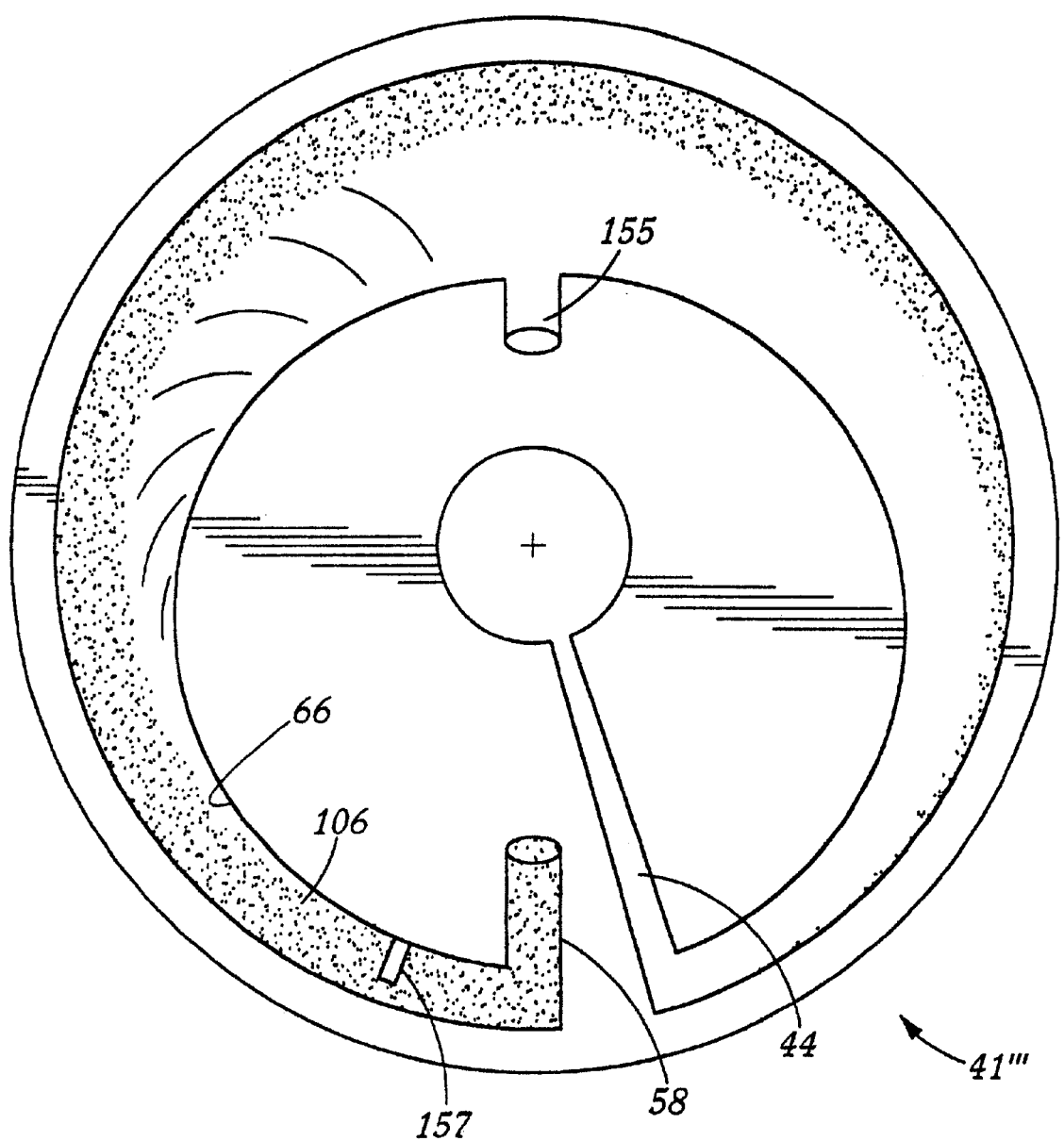
FIG. 11 is a plan view of a further alternative embodiment of the present invention.
Figure 12:
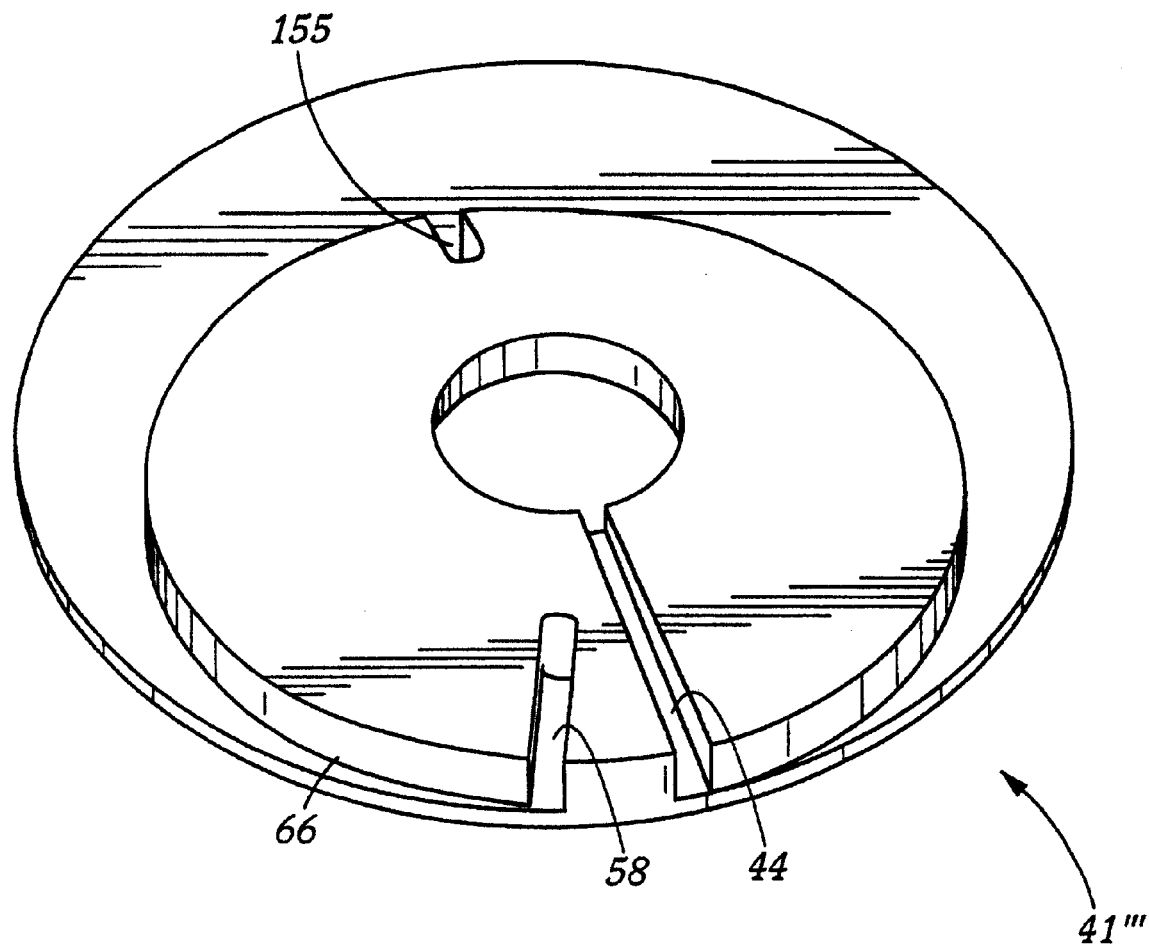
FIG. 12 is an isometric view of an alternative embodiment of a separation layer like that shown in FIG. 11.

The embodiment of FIGS. 11 and 12 is directed to a similar weight balance concept. However, in the embodiment of FIGS. 11 and 12, less plasma is relegated to a substantially static disposition as within the channel 150 of FIG. 10. Rather, here, a shortened channel 155 is disposed to receive the exit flow of plasma from the separation configuration 41'''. Then, more plasma is allowed to be in relative continually flowing disposition around the configuration 41''' even though the removal of the plasma outflow tube to the substantially opposite side of the rotor may encourage a substantially no or low flow condition at the meeting position of interface 106 with wall 66. A further alternative here is the use of an optional wall 157 to ensure the location of the interface does not run too far radially outwardly. This wall 157 is not shown in the isometric view of FIG. 12 to underscore the optional nature thereof.

Note also, FIGS. 9 and 12 are shown without exterior walls such as wall 67 in FIGS. 3A, 3B and 5, for example. This is shown this way for convenience in demonstrating the internal components of these alternative rotors. An exterior wall such as wall 67 would be preferred in these embodiments as well.

Figure 13:
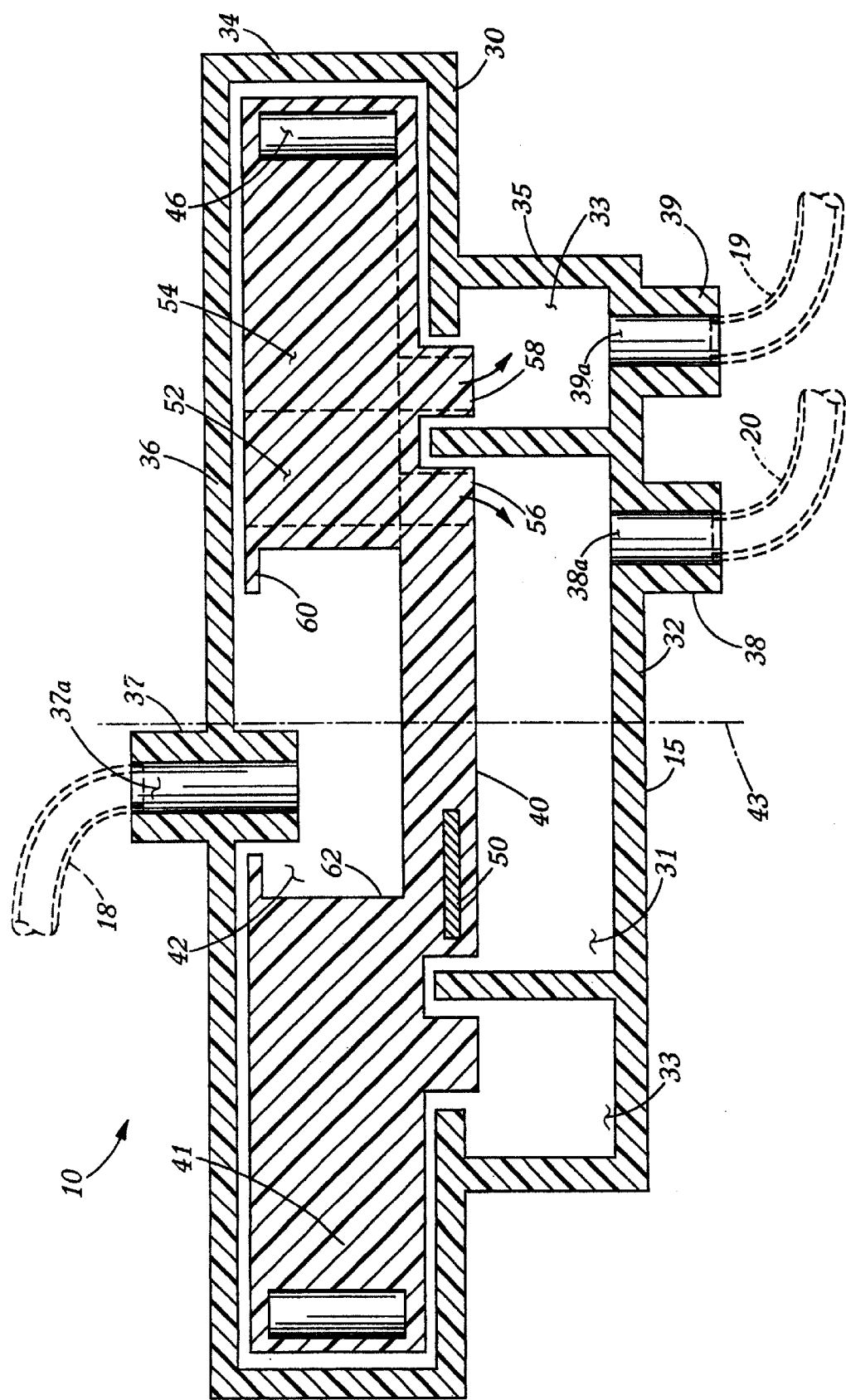
FIG. 13 is a cross-sectional view like that of FIG. 2 of an alternative embodiment of a centrifuge unit of the present invention.
Figure 14:
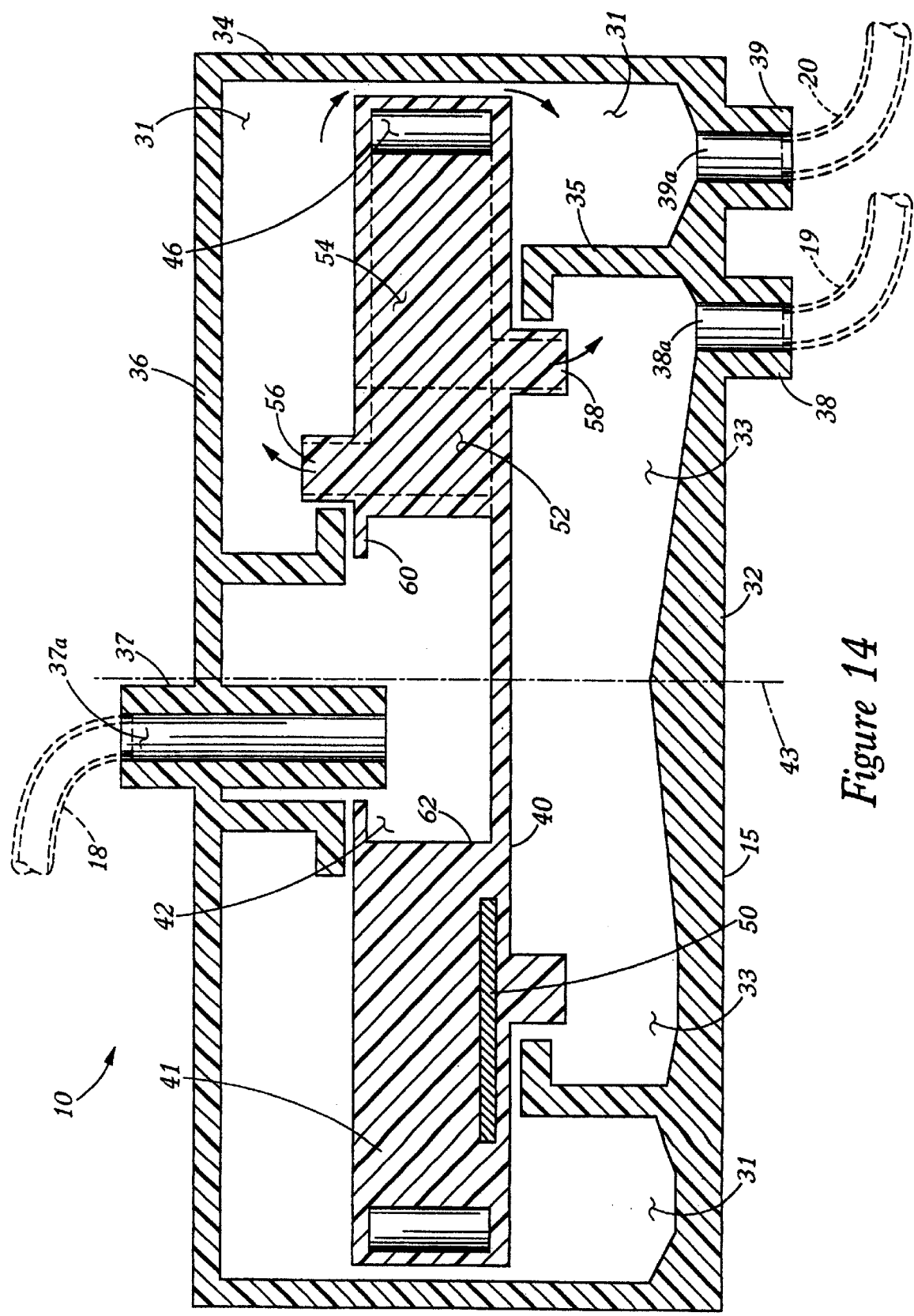
FIG. 14 is a cross-sectional view like that of FIG. 2 of an alternative embodiment of a centrifuge unit of the present invention.

In two further alternative embodiments as depicted in more detail in FIGS. 13 and 14, the centrifuge units 14 generally include similar outer housings 30 and corresponding internal rotor assemblages 40. In broad terms, each outer housing 30 includes a bottom wall 32 (the exterior face of which being the flat-bottom surface 15 described above), one or more circumferential walls 34, 35, and a top wall 36. As before, bottom, circumferential, and top walls 34, 35 and 36 are preferably contiguous (after assembly with a rotor 40) and may at least partially be integrally conjoined or formed, although they may each be separately-formed elements which are subsequently joined. In either case, the walls preferably form a fluid-tight arrangement. A fluid inlet aperture 37*a* is preferably defined in the top wall 36, and two exit 38*a*, 39*a* are preferably defined in and through the bottom wall 32 (although these could be disposed in and through a side wall 34 or 35). Respective inlet and outlet structures 37, 38 and 39 as shown are preferably used to define the respective apertures 37*a*, 38*a* and 39*a*, although other forms could be used. The tubing system 16 and respective fluid storage containers 22, 24 for example, may be connected to the housing 30 as shown in FIGS. 1A and 1B (and in dashed lines in FIGS. 13 and 14) via the connections of tubing lines 18, 19 and 20 with the respective aperture structures 37, 38 and 39; however, in these embodiments, the bags 22, 24 are preferably disposed below the unit 14 to allow for gravity drainage therefrom into the bags 22, 24.

The rotor 40 in FIGS. 13 and 14, also as above; particularly includes an outlet channel 52 which then connects to an outlet aperture 56 and an outlet channel 54 which similarly connects to an outlet aperture 58. However, FIGS. 13 and 14 show an embodiment wherein the plasma outlet 56 leads first vertically downwardly through the rotor 40 and then it extends downwardly from the rotor 40. This thus provides fluid communication from the outlet to the lower interior channel 31 of the housing 30. In this way then, fluid passing through outlet 56 then empties from the rotor 40 into the rotor housing 30 within the lower channel 31 thereof. Lower channel 31 is then also in fluid flow communication with the outlet 38 which thereby allows for fluid flow out of housing channel 31 into and through outlet 38, and from there, into and through tubing line 20 ultimately to fluid container 24 (see Fig. where however, the container 24 is preferably disposed below the unit 14 so that separated fluid can flow under the force of gravity from chamber 31 to the container 24.

Similarly, as shown in FIGS. 13 and 14, the RBC outlet 58 also leads downwardly through the rotor 40 and communicates outwardly to and provides fluid communication from the RBC outlet 58 to an intermediate interior circumferential channel 33 of the housing 30. Fluid then passes through outlet 58 and then empties from the rotor 40 into the intermediate channel 33 within the rotor housing 30. Channel 33 is then also in fluid flow communication with the RBC outlet 39 thus allowing for fluid flow out of channel 33 into and through outlet 39, and from there, into and through tubing line 19 ultimately to fluid container 22 (again, see FIG. 1A). Moreover, as was true above, the fluid reaching the interior channel 33 is preferably drained by the pull of gravity, into a hanging storage bag 22 which here also is preferably disposed below the centrifugal unit 14.

Also note in FIGS. 13 and 14, a piece of metallic material 50 is shown disposed within the lower part of rotor 40. At least one such piece of metallic material 50 is preferably disposed therein to interact with the rotating magnetic field generated by the base to spin the rotor 40 about the rotational axis 43 (see description below) within the substantially stationary housing 30.

In view of the foregoing, various modifications, adaptations and variations of the structure and methodology of the present invention will become apparent to those skilled in the art without departing from the scope or spirit of the present invention. It is intended that the present invention cover all such modifications, adaptations and variations as limited only by the scope of the following claims and their equivalents.

The invention claimed is:

1. A method for centrifugally separating a composite fluid into at least two of the component fluid parts thereof, said method comprising receiving a composite fluid front a fluid source in a separation layer having a fluid receiving area adjacent an axis of rotation, said separation layer having:
   a fluid inlet channel having an inlet channel height;
   a circumferential fluid separation channel, said separation channel having a proximal end and a distal end; and,
   a first separated fluid outlet channel having a first height;
   a second separated fluid outlet channel having a second height, said second outlet channel being adjacent said distal end of said separation channel and said first outlet channel being proximal from said second channel, wherein said second height is less than said first height and said first height is less than said inlet channel height;

placing said inlet channel in fluid communication with said fluid receiving area; and placing said circumferential separation channel in fluid communication with said fluid inlet channel adjacent said proximal end of said separation channel and with each of said separated fluid outlet channels; and placing at least one separated fluid outlet channels in fluid communication with a corresponding separated component fluid receiver; and delivering at least one separated fluid component to a separated component fluid receiver.

2. A method according to claim 1 in which the relationship of the respective inlet and outlet positions of said inlet and said at least one separated fluid outlet channels to each other provides a fluid pressure imbalance.

3. A method according to claim 1 further comprising placing the respective inlet and outlet positions of said inlet and said at least one separated fluid outlet channels to provide a fluid pressure imbalance which provides fluid flow control by driving the flow of a composite fluid and at least one component thereof forward from the receiving area, respectively through the inlet, circumferential and at least one outlet channels.

4. A method according to claim 1 further comprising placing the respective inlet and outlet positions of said inlet and said at least one separated fluid outlet channels to each other to provide a fluid pressure imbalance for respective fluids flowing through the respective inlet and at least one outlet channels, and is defined as:

$$\rho_1 g_1 h_1 > \rho_2 g_2 h_2:$$

wherein the first position, $h_1$, represents the relative radial height of the inlet channel, and the second position, $h_2$, represents the relative radial height of the first outlet channel, wherein $g_1$ and $g_2$ are centrifugal acceleration values and $\rho_1$ represents the density of the fluid in the inlet channel and $\rho_2$ represents the density of the fluid in the least one outlet channel.

5. A method according to claim 1 wherein the inlet position of the inlet channel is designated as $h_1$ and, wherein the outlet position of the first outlet channel is $h_2$, and the outlet position of the second outlet channel is $h_3$, and wherein $g_1 g_2$ and $g_3$ are centrifugal values, and $\rho_1$ represents the density of the fluid in the fluid inlet channel, $\rho_2$ represents the density of the fluid in the first outlet channel, and $\rho_3$ represents the density of the fluid in the second outlet channel, and whereby these structural values are related to each other such that the inlet channel fluid dynamic pressure, $\rho_1 g_1 h_1$, is greater than either of the two outlet fluid dynamic pressures, $\rho_2 g_2 h_2$ and $\rho_3 g_{3h3}$, as in;

$$\rho_1 g_1 h_1 > \rho_2 g_2 h_2 \text{ or, } \rho_1 g_1 h_1 > \rho_3 g_3 h_3;$$

so that fluid will flow from the fluid receiving area through the respective first and second outlet channels.

6. A method according to claim 5 wherein the ρgh values may be incrementally summed such that:

$$\Sigma(\rho g h)_1 > \Sigma(\rho g h)_2,$$

or, $$\Sigma(\rho g h)_1 > \Sigma(\rho g h)_3.$$

7. A method according to claim 5 wherein the ρ values are different for each term in the relationship such that the first ρ value, in $\rho_1 g_1 h_1$, is the density of the inlet composite fluid to be separated, whereas, the second and third ρ values, appearing in $\rho_2 g_2 h_2$ and $\rho_3 g_3 h_3$ represent the densities of respective first and second separated fluid components.

8. A method according to claim 5 wherein the ρ values are different for each term in the relationship such that the first ρ value, in $\rho_1 g_1 h_1$, is the density of the inlet composite fluid to be separated, the second and third ρ values, appearing in $\rho_2 g_2 h_2$ and $\rho_3 g_3 h_3$, represent the densities of respective first and second separated fluid components, and $\rho_2 g_2 h_2$ and $\rho_3 g_3 h_3$ equalize with each other.

9. A method according to claim 5 wherein the composite fluid to be separated is blood and the ρ values are different for each term in the relationship such that the first ρ value, in $\rho_1 g_1 h_1$, is the density of a whole blood composite fluid, whereas, the second and third ρ values, appearing in $\rho_2 g_2 h_2$ and $\rho_3 g_3 h_3$, represent the densities of respective separated blood components.

10. A method according to claim 5 wherein the ρ values are different for each term in the relationship such that the first ρ value, in $\rho_1 g_1 h_1$, is the density of the inlet composite fluid to be separated, whereas, the second and third ρ values, appearing in $\rho_2 g_2 h_2$ and $\rho_3 g_3 h_3$, represent the densities of respective first and second separated fluid components; and the second ρ value in $\rho_2 g_2 h_2$ includes first and second elements from the respective first and second separated fluid components, such that $\rho_2 g_2 h_2$ is the sum of $\rho_{1stcomponent} g_{1stcomponent}(h_2-h_i)$ and $\rho_{2ndcomponent} g_{2ndcomponent} h_i$; wherein $h_i$ is the height of the interface between the first and second separated fluid components.

11. A method according to claim 10 wherein the composite fluid to be separated is blood and the ρ values are different for each term in the relationship such that the first ρ value, in $\rho_1 g_1 h_1$, is the density of whole blood, whereas, the respective first and second separated fluid ρ values, appearing in $\rho_{1stcomponent} g_{1stcomponent}(h_2-h_i)$ and $\rho_{2ndcomponent} g_{2ndcomponent} h_i$; represent the densities of the separated components, plasma and red blood cells (RBCs), respectively.

12. A method according to claim 1 further comprising selecting the respective first and second lengths of said first and second separated fluid outlet channels to each other to provide a substantial fluid pressure balance for respective fluids flowing therethrough.

13. A method according to claim 1 further comprising selecting the respective first and second lengths of said first and second separated fluid outlet channels to each other to provide a substantial fluid pressure balance for respective fluids flowing through the respective first and second outlet channels, and is defined such that it provides fluid flow control of the interface of separated fluid components within the circumferential separation channel.

14. A method according to claim 1 further comprising selecting the respective first and second lengths of said first and second separated fluid outlet channels to each other to provide a substantial fluid pressure balance for respective fluids flowing through the respective first and second outlet channels, and is defined as:

$$\rho_2 g_2 h_2 = \rho_3 g_3 h_3$$

wherein the first length of the first outlet channel is $h_2$, and the second length of the second outlet channel is $h_3$, wherein g is a gravitational acceleration value and $\rho_2$ represents the density of the fluid in the first outlet channel and $\rho_3$ represents the density of the fluid in the second outlet channel.

15. A method according to claim 14 wherein the ρgh values may be incrementally summed such that $\Sigma(\rho g h)_2 = \Sigma(\rho g h)_3$.

16. A method according to claim 14 in which the composite fluid to be separated is blood and the first and second separated components are plasma and red blood cells (RBCs), respectively.

17. A method according to claim 14 in which the $\rho_2$ value in the $\rho_2 g_2 h_2$ term has two distinct components derived from a combination of separated fluid component terms such that $\rho_2 g_2 h_2$ is the sum of $\rho_{1stcomponent} g_{1stcomponent}(h_2-h_i)$ and a $\rho_{2ndcomponent} g_{2ndcomponent} h_i$; whereby $h_i$ is the height of the interface between the first and second separated fluids, and, $$\rho_2 g_2 h_2 = \rho_{1stcomponent} g_{1stcomponent}(h_2-h_i) + \rho_{2ndcomponent} g_{2ndcomponent} h_i = \rho_{2ndcomponent} g_{2ndcomponent} h_3 = \rho_3 g h_3.$$

18. A method according to claim 14 in which the composite fluid to be separated is blood and the first and second separated components are plasma and red blood cells (RBCs); and wherein the $\rho_2$ value in the $\rho_2 g h_2$ term has two distinct components derived from a combination of separated fluid component terms, thus having a plasma and an RBC component such that $\rho_2 g_2 h_2$ is the sum of $\rho_{plasma} g_{plasma}(h_2-h_i)$ and a $\rho_{RBC} g_{RBC} h_i$ portion; wherein $h_i$ is the height of the interface between the RBCs and the plasma, and, $$\rho_2 g_2 h_2 = \rho_{plasma} g_{plasma}(h_2-h_i) + \rho_{RBC} g_{RBC} h_i = \rho_{RBC} g_{RBC} h_3 = \rho_3 g_3 h_3.$$

19. A method according to claim 18 wherein the composite fluid to be separated as blood and the ρ values are different for each term in the relationship such that the first ρ value, in $\rho_1 g_1 h_1$, is the density of whole blood, whereas, the second and third ρ values, appearing in $\rho_2 g_2 h_2$ and $\rho_3 g_3 h_3$, represent the densities of the first and second separated components, plasma and red blood cells (RBCs).

20. A method according to claim 14 wherein the inlet position of the inlet channel is designated as $h_1$ and wherein the first outlet position of the first outlet channel is $h_2$, and the second outlet position of the second outlet channel is $h_3$, wherein $g_1$, $g_2$ and $g_3$ are centrifugal values and $\rho_1$ represents the density of the fluid in the fluid inlet channel, $\rho_2$ represents the density of the fluid in the first outlet channel, and $\rho_3$ represents the density of the fluid in the second outlet channel and these values are related to each other such that the inlet fluid dynamic pressure, $\rho_1 g_1 h_1$, is greater than the either of the two outlet fluid dynamic pressures, $\rho_2 g_2 h_2$ and $\rho_3 g_3 h_3$, as in:

$$\rho_1 g_1 h_1 > \rho_2 g_2 h_2 \text{ or } \rho_3 g_3 h_3$$

so that fluid will flow from the inlet toward the outlets.

21. A method according to claim 20 wherein the ρ values are different for each term in the relationship such that the first ρ value, in $\rho_1 g_1 h_1$, is the density of the inlet composite fluid to be separated, whereas, the second and third ρ values, appearing in $\rho_2 g_2 h_2$ and $\rho_3 g_3 h_3$, represent the densities of the respective first and second separated fluid components.

22. A method according to claim 1 further comprising delivering the separated fluid component to at least one separated fluid outlet channel such that the separated fluid component retains kinetic energy to flow to the corresponding separated component fluid receiver.

23. A method according to claim 22 in which the kinetic energy is retained by action of a vortex pump configuration.

24. A method according to claim 1 further comprising providing a balance channel which is disposed in fluid communication with the circumferential channel, said balance channel being between said proximal end of said circumferential channel and said first channel and having a geometry that counterbalances said first and second outlet channels, whereby said balance channel may provide a weight balance to said configuration relative to said inlet channel and the at least one outlet channel.

* * * * *